(12) United States Patent
Fadli

(10) Patent No.: US 7,288,124 B2
(45) Date of Patent: Oct. 30, 2007

(54) HETEROAROMATIC BINUCLEAR BLACK DIRECT DYES

(75) Inventor: Aziz Fadli, Chelles (FR)

(73) Assignee: L'Oreal S.A., Paris (FR)

( * ) Notice: Subject to any disclaimer, the term of this patent is extended or adjusted under 35 U.S.C. 154(b) by 237 days.

(21) Appl. No.: 11/220,688

(22) Filed: Sep. 8, 2005

(65) Prior Publication Data

US 2006/0053568 A1   Mar. 16, 2006

Related U.S. Application Data

(60) Provisional application No. 60/619,696, filed on Oct. 19, 2004.

(51) Int. Cl.
*A61K 7/13* (2006.01)
(52) U.S. Cl. .............. 8/405; 8/406; 8/410; 8/411; 8/421; 546/262; 544/105
(58) Field of Classification Search ............... 8/405, 8/406, 410, 411, 421; 546/262; 544/105
See application file for complete search history.

(56) References Cited

U.S. PATENT DOCUMENTS

| | | | |
|---|---|---|---|
| 4,734,418 A * | 3/1988 | Yokoyama et al. | .... 514/252.16 |
| 5,364,414 A | 11/1994 | Lang et al. | |
| 5,380,340 A | 1/1995 | Neunhoeffer et al. | |
| 5,708,151 A | 1/1998 | Möckli | |
| 5,785,717 A | 7/1998 | Maubru et al. | |
| 6,099,592 A | 8/2000 | Vidal et al. | |
| 6,248,137 B1 | 6/2001 | Terranova et al. | |
| 6,338,741 B1 | 1/2002 | Vidal et al. | |
| 6,379,397 B2 | 4/2002 | Vidal et al. | |
| 6,613,313 B2 | 9/2003 | Kimura | |
| 6,645,258 B2 | 11/2003 | Vidal et al. | |
| 6,783,558 B2 | 8/2004 | Pratt et al. | |
| 6,837,908 B2 | 1/2005 | Vidal et al. | |
| 6,855,827 B2 | 2/2005 | Vidal et al. | |
| 2001/0020310 A1 | 9/2001 | Terranova et al. | |
| 2002/0007520 A1 | 1/2002 | Vidal et al. | |
| 2002/0050013 A1 | 5/2002 | Vidal et al. | |
| 2002/0152558 A1 | 10/2002 | Vidal et al. | |
| 2002/0197223 A1 | 12/2002 | Kimura | |
| 2003/0019051 A9 | 1/2003 | Vidal et al. | |
| 2003/0024059 A1 | 2/2003 | Pratt et al. | |
| 2003/0163876 A1 | 9/2003 | Vidal et al. | |
| 2005/0015893 A1 | 1/2005 | Fessmann et al. | |

FOREIGN PATENT DOCUMENTS

| | | |
|---|---|---|
| DE | 25 54 456 | 6/1977 |
| DE | 26 13 707 | 10/1977 |
| DE | 25 16 117 C2 | 8/1984 |
| DE | 41 33 957 A1 | 4/1993 |
| DE | 196 19 112 A1 | 11/1997 |
| EP | 0 424 261 B1 | 4/1991 |
| EP | 0 714 954 B1 | 6/1996 |
| EP | 0 728 464 B1 | 8/1996 |
| EP | 0 740 931 B1 | 11/1996 |
| EP | 0 923 929 B1 | 6/1999 |
| EP | 0 926 149 B1 | 6/1999 |
| EP | 1 166 754 A2 | 1/2002 |
| EP | 1 275 367 A1 | 1/2003 |
| EP | 1 459 732 A1 | 9/2004 |
| FR | 1 397 551 | 3/1965 |
| FR | 2 733 249 A1 | 11/1996 |
| FR | 2 771 631 A1 | 6/1999 |
| FR | 2 827 601 A1 | 1/2003 |
| FR | 2 832 148 A1 | 5/2003 |
| JP | 11-158047 | 6/1999 |
| WO | WO 95/01772 | 1/1995 |
| WO | WO 95/15144 | 6/1995 |

OTHER PUBLICATIONS

STIC Search Report dated Jun. 6, 2007.*
French Search Report for FR 0451987 (French Priority Application for U.S. Appl. No. 11/220,688, the present application) dated May 3, 2005.
English language Derwent Abstract of DE 25 16 117 C2, Aug. 16, 1984.
English language Derwent Abstract of DE 25 54 456, Jun. 16, 1977.
English language Derwent Abstract of DE 26 13 707, Oct. 13, 1977.
English language Derwent Abstract of DE 196 19 112 A1, Nov. 13, 1997.

* cited by examiner

*Primary Examiner*—Eisa Elhilo
(74) *Attorney, Agent, or Firm*—Finnegan, Henderson, Farabow, Garrett & Dunner LLP

(57) ABSTRACT

Disclosed herein are novel heteroaromatic binuclear direct dyes, dye compositions containing these dyes and also a process for dyeing keratin fibers using them. In particular, the invention relates to heteroaromatic binuclear direct dyes comprising a pyridine nucleus.

With these novel dyes, black shades that show good fastness can be obtained, and they also may show good stability in dye compositions.

45 Claims, No Drawings

HETEROAROMATIC BINUCLEAR BLACK DIRECT DYES

This application claims benefit of U.S. Provisional Application No. 60/619,696, filed Oct. 19, 2004, the contents of which are incorporated herein by reference. This application also claims benefit of priority under 35 U.S.C. § 119 to French Patent Application No. 04 51987, filed Sep. 8, 2004, the contents of which are also incorporated by reference.

The present disclosure relates to novel heteroaromatic binuclear direct dyes, to dye compositions containing these dyes and to the process for dyeing keratin fibers using them. In particular, the present disclosure relates to heteroaromatic binuclear direct dyes comprising a pyridine nucleus.

It is known practice to dye keratin fibers, such as human hair, with dye compositions containing direct dyes. The standard dyes that are used are, for example, dyes of the nitrobenzene, anthraquinone, nitropyridine, azo, cationic azo, xanthene, acridine, azine, and triarylmethane nitrobenzene type or natural dyes.

These dyes, which are colored and coloring molecules that show affinity for fibers, are typically applied to keratin fibers for the time required to obtain the desired coloration, and then rinsed out. The colorations resulting therefrom, while particularly chromatic colorations, are, however, temporary or semi-permanent since the nature of the interactions that link the direct dyes to the keratin fiber, and their desorption from the surface and/or from the core of the fiber give them relatively weak dyeing power and may result in poor wash-fastness or resistance to perspiration. These direct dyes may also be light-sensitive due to the relatively poor resistance of the chromophore to photochemical attack, and this may lead to fading of the coloration of the hair over time.

European patent application EP 1 166 754 describes a dye composition comprising cationic phenazinium azo direct dyes. Due to the presence of the azo function, these compounds may be unstable when placed in contact with a reducing agent such as erythorbic acid, metabisulfite or sulfite, this instability being reflected in destruction of the chromophoric system.

Thus it would be desirable to provide novel direct dyes that do not have some or all of the drawbacks of the prior art, for example to provide direct dyes that allow dark, black to grey, shades to be obtained, which are light-fast, and/or resistant to bad weather, washing and perspiration, and/or are also stable in a standard dyeing medium.

It would also be desirable to provide black direct dyes allowing hair to be dyed in shades ranging from grey to black, without the need to lighten the hair beforehand, and also black direct dyes which, even when fading, do not change shade, for example by changing color after the action of washing, light or sweat towards shades with blue, violet, red, green, etc. glints. Finally, these black direct dyes should ideally make it possible to maintain, after several applications, the shade obtained during the first application.

Disclosed herein, therefore, is, in one embodiment, a dye composition comprising, in a suitable medium, a compound of formula (I) below:

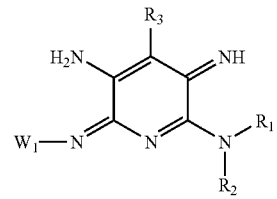

in which
R$_3$ is chosen from:
a hydrogen atom,
a linear or branched C$_1$-C$_{10}$ hydrocarbon-based chain, which can form at least one 5- to 8-membered carbon-based ring, and which may be saturated or unsaturated, wherein at least one carbon atom of the carbon-based chain may be replaced with an entity chosen from oxygen, nitrogen and sulfur atoms and SO$_2$ groups, and wherein the carbon atoms may be, independently of each other, substituted with at least one halogen atom; R$_3$ not comprising a peroxide bond or diazo, nitro or nitroso radicals, R$_3$ not being linked to the pyridine ring via an oxygen, nitrogen or sulfur atom;

R$_1$ and R$_2$ are chosen from, independently of each other:
a hydrogen atom,
a linear or branched C$_1$-C$_{10}$ hydrocarbon-based chain, which can form at least one 5- to 8-membered carbon-based ring, and which may be saturated or unsaturated, wherein at least one carbon atom of the carbon-based chain may be replaced with an entity chosen from oxygen, nitrogen and sulfur atoms and SO$_2$ groups, and wherein the carbon atoms may be, independently of each other, substituted with at least one halogen atom; R$_1$ and R$_2$ not comprising a peroxide bond or diazo, nitro or nitroso radicals, and R$_1$ and R$_2$ not being directly linked to the nitrogen atom via an oxygen, sulfur or nitrogen atom
a cationic radical -D-Z in which Z is an onium radical and D is a linear or branched C$_1$-C$_{14}$ hydrocarbon-based chain, which can form at least one 5- to 8-membered carbon-based ring, and which may be saturated or unsaturated, wherein at least one carbon atom of the carbon-based chain may be replaced with an entity chosen from oxygen, nitrogen and sulfur atoms and SO$_2$ groups; the arm D not being linked to the nitrogen atom via a nitrogen, oxygen or sulfur atom, or R$_1$ and R$_2$ form, together with the nitrogen atom to which they are attached, a ring of formula (IV):

(IV)

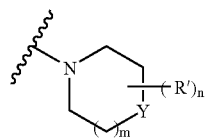

in which
R' is chosen from:
a halogen atom such as fluorine, chlorine or bromine;
a C$_1$-C$_4$ alkyl radical optionally substituted with at least one radical chosen from hydroxyl, carboxyl, C$_1$-C$_4$ alkoxycarbonyl, (C$_1$-C$_4$)alkylamido((C$_1$-C$_4$)alkyl-CONH—), (C$_1$-C$_4$)alkylNHCO—), (C$_1$-C$_4$)alkylsulfonyl (($C_1$-$C_4$)alkyl$SO_2$—), $C_1$-$C_4$ alkoxy, ($C_1$-$C_4$) alkylsulfonamido (($C_1$-$C_4$)alkyl$SO_2$NH—) and ($C_1$-$C_4$)alkylsulfamoyl (($C_1$-$C_4$)alkylNH$SO_2$—) radicals;

NR'$_3$R'$_4$ with R'$_3$ and R'$_4$, which may be identical or different, being chosen from a hydrogen atom, $C_1$-$C_4$ alkyl radicals optionally substituted with at least one radical chosen from hydroxyl, $C_1$-$C_4$ alkoxy, amino, mono- or dialkylamino, ($C_1$-$C_4$)alkylCO—, ($C_1$-$C_4$)alkylNHCO— and ($C_1$-$C_4$)alkyl$SO_2$ radicals;

a carboxyl radical;

a $C_1$-$C_4$ alkoxycarbonyl radical;

a ($C_1$-$C_4$)alkylamido radical (($C_1$-$C_4$)alkylCONH—);

a ($C_1$-$C_4$)alkylsulfonyl radical (alkyl$SO_2$—);

an alkylsulfonamido radical (($C_1$-$C_4$)alkyl$SO_2$NH—);

a hydroxyl radical;

a $C_1$-$C_4$ alkoxy radical;

a $C_2$-$C_4$ hydroxyalkoxy radical;

a ($C_1$-$C_4$)alkylcarboxamido radical (($C_1$-$C_4$)alkylNHCO—);

—($C_1$-$C_4$)alkylsulfamoyl (($C_1$-$C_4$)alkyl-NH—$SO_2$—);

a $C_1$-$C_4$ thioether radical;

a sulfonic radical ($SO_3H$), which may be in salt form;

a cationic radical -D1-Z in which D1 is a covalent bond or D, n is an integer ranging from 0 to 12, m is an integer ranging from 0 to 2, Y is chosen from a carbon atom, an oxygen atom, a radical NR'$_5$ and a radical NR'$_6$R'$_7$ with R'$_5$ having the same meaning as R'$_3$; R'$_6$ and R'$_7$ have the same meaning as R'$_3$ and are other than a hydrogen atom, with the proviso that when n>1, the radicals R' may be different from each other, $W_1$ is an aromatic heterocyclic radical chosen from the following radicals

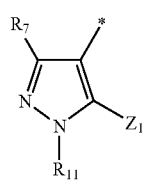

(RI)

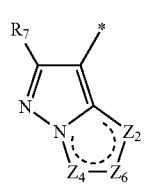

(RII)

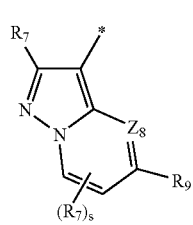

(RIII)

-continued

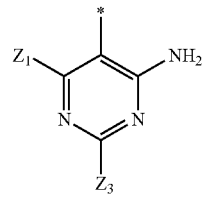

(RIV)

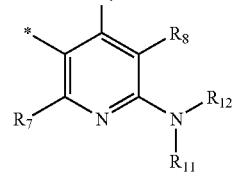

(RV)

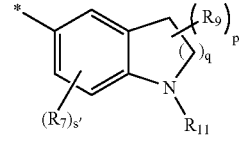

(RVI)

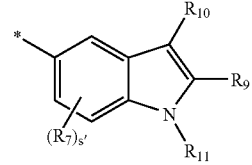

(RVII)

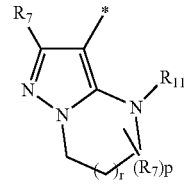

(RVIII)

in which
s is 0, 1 or 2,
s' is 0, 1, 2 or 3,
$Z_1$ and $Z_3$ are chosen, independently of each other, from hydroxyl and $NR_{11}R_{12}$ radicals,
$Z_2$, $Z_4$ and $Z_6$ are chosen from, independently of each other, nitrogen atoms, radicals $CR_{12}$ or radicals $NR_{11}$, with the proviso that at least one of $Z_2$, $Z_4$ and $Z_6$ represents a radical $CR_{12}$ and that there are not more than 3 contiguous nitrogen atoms,
$Z_8$ is chosen from a nitrogen atom or a radical $CR_{12}$,
$R_6$ and $R_8$, independently of each other, have the same meanings as $R_3$,
$R_7$, $R_9$, $R_{10}$, $R_{11}$, and $R_{12}$ are chosen from, independently of each other:
a hydrogen atom,
linear or branched $C_1$-$C_{10}$ hydrocarbon-based chains, which can each form at least one 5- to 8-membered carbon-based ring, and which may be saturated or unsaturated, wherein at least one carbon atom of the carbon-based chain may be replaced with an entity chosen from oxygen, nitrogen and sulfur atoms and $SO_2$ groups, and wherein the carbon atoms may be, independently of each other, substituted with at least one halogen atom; the radicals $R_7$ and $R_9$ to $R_{12}$ not comprising a peroxide bond or diazo or nitroso radicals, and the radicals $R_{11}$ and $R_{12}$ not being directly linked to the nitrogen atom via an oxygen, sulfur or nitrogen atom, with the proviso that the radicals $R_7$ and $R_9$ may be independent of each other, p may take the values 4 to 8, q may take the values 1 to 3, and r may take the values 0 to 2,

* indicates the point of attachment of $W_1$ in formula (I), with the proviso that the compound of formula (I) cannot comprise more than one D1-Z radical.

Also disclosed herein is a dye composition containing, in a suitable medium, at least one direct dye of the present disclosure. The composition of the present disclosure is particularly useful for dyeing keratin fibers, such as human keratin fibers.

When, in the definition of $Z_2$, $Z_4$ and $Z_6$ that are chosen from, independently of each other, nitrogen atoms and radicals $CR_{12}$ and radicals $NR_{11}$, it is specified that there cannot be more than 3 contiguous nitrogen atoms, this means that it is not possible, for example, to obtain the following structure

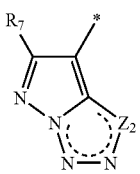

Furthermore, unless otherwise mentioned, the limits delimiting the breadth of a range of values are included in that range of values.

In the context of the present disclosure, the compounds of formula (I) are not only those described by formula (I), but any other tautomeric form, for instance the following tautomeric form:

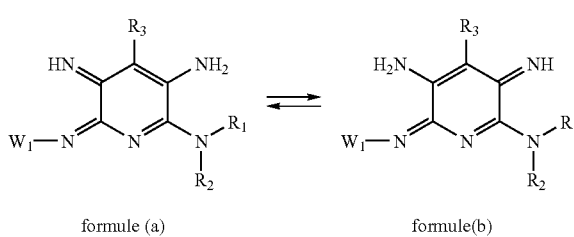

formule (a)    formule(b)

In the examples that are given in the description hereinbelow, only one of these tautomeric forms will be indicated.

In formula (I), $R_3$ is, in at least one embodiment, chosen from a hydrogen atom and a $C_1$-$C_4$ alkyl radical optionally substituted with at least one radical chosen from hydroxyl, $C_1$-$C_2$ alkoxy, amino and $C_1$-$C_2$ (mono)- or (di)alkylamino radicals. By way of example, $R_3$ is chosen from a hydrogen atom and from methyl, ethyl and 2-hydroxyethyl radicals and, in at least one embodiment is chosen from a hydrogen atom and a methyl radical.

In at least one embodiment, the radicals $R_1$ and $R_2$ may be chosen, independently, from hydrogen and a $C_1$-$C_6$ alkyl radical optionally substituted with a hydroxyl, an alkoxy, an amino, a $C_1$-$C_4$ (mono)- or (di)alkylamino, or a radical -D-Z with Z possibly being an imidazolium, a tri($C_1$-$C_4$)alkylammonium, a pyridinium or a piperidinium. By way of example, $R_1$ and $R_2$ are chosen from hydrogen, methyl, ethyl, hydroxyethyl, propyl, propylimidazolium and propyltrimethylammonium radicals.

When $R_1$ and $R_2$ form, with the nitrogen atom to which they are attached, a 5- to 8-membered heterocycle of formula (IV), this heterocycle may be chosen, in at least one embodiment, from pyrrolidine, piperidine, homopiperidine, piperazine, homopiperazine and diazepane heterocycles. By way of example, the heterocycle is chosen from pyrrolidine, 3-hydroxypyrrolidine, 3-aminopyrrolidine, 3-N,N-dimethylaminopyrrolidine, 3-acetamidopyrrolidine, 3-(methylsulfonylamino)pyrrolidine, proline, 3-hydroxyproline, 3-(N-methylimidazolium)pyrrolidine, 3-(tri ($C_1$-$C_4$) alkylammonium)pyrrolidine, piperidine, hydroxypiperidine, homopiperidine, diazepane, N-methylhomopiperazine and N-β-hydroxyethylhomopiperazine, and the addition salts thereof. For example, in at least one embodiment, $R_1$ and $R_2$ form, with the nitrogen atoms to which they are attached, an optionally substituted pyrrolidine ring. According to at least one embodiment, R' may be a radical -D1-Z chosen from an imidazolium and a trialkylammonium.

The radicals $R'_5$, $R'_6$ and $R'_7$ may, in at least one embodiment, be a $C_1$-$C_4$ alkyl.

The radicals $R'_3$ and $R'_4$ may, in at least one embodiment, be chosen from ($C_2$-$C_4$)alkylimidazolium, ($C_2$-$C_4$)alkylpyridinium and ($C_2$-$C_4$)alkyltri($C_2$-$C_4$)alkylammonium radicals.

The cationic radical -D-Z may be represented by formula (V) below

in which

D is as defined above, $R_{17}$, $R_{18}$ and $R_{19}$, independently of each, are chosen from $C_1$-$C_{15}$ alkyl radicals; $C_1$-$C_6$ monohydroxyalkyl radicals; $C_2$-$C_6$ polyhydroxyalkyl radicals; ($C_1$-$C_6$)alkoxy ($C_1$-$C_6$)alkyl radicals; aryl radicals; benzyl radicals; $C_1$-$C_6$ amidoalkyl radicals; tri($C_1$-$C_6$)alkylsilane($C_1$-$C_6$)alkyl radicals; $C_1$-$C_6$ aminoalkyl radicals; and $C_1$-$C_6$ aminoalkyl radicals in which the amine is mono- or disubstituted with at least one radical chosen from $C_1$-$C_4$ alkyl, ($C_1$-$C_6$)alkylcarbonyl, acylamino and ($C_1$-$C_6$)alkylsulfonyl radicals;

$R_{17}$, $R_{18}$ and $R_{19}$ together, in pairs, may form, with the quaternized nitrogen atom to which they are attached, a 5-, 6- or 7-membered carbon-based saturated ring which may comprise at least one hetero atom, the cationic ring possibly being substituted with at least one substituent chosen from halogen atoms, hydroxyl radicals, $C_1$-$C_6$ alkyl radicals, $C_1$-$C_6$ monohydroxyalkyl radicals, $C_2$-$C_6$ polyhydroxyalkyl radicals, $C_1$-$C_6$ alkoxy radicals, tri($C_1$-$C_6$)alkylsilane($C_1$-$C_6$)alkyl radicals, amido radicals, carboxyl radicals, $C_1$-$C_6$ alkylcarbonyl radicals, thio radicals, $C_1$-$C_6$ thioalkyl radicals, ($C_1$-$C_6$)alkylthio radicals, amino radicals, and amino radicals mono- or disubstituted with at least one radical chosen from ($C_1$-$C_6$)alkyl, ($C_1$-$C_6$)alkylcarbonyl, acylamino and ($C_1$-$C_6$)alkylsulfonyl radicals;

one from among $R_{17}$, $R_{18}$ and $R_{19}$ may be linked to one of the carbon or nitrogen atoms of the arm D to form a 5- to 7-membered ring, and $X^-$ is a counterion.

$X^-$ is chosen from an organic or mineral anion chosen, for example, from a halide such as chloride, bromide, fluoride or iodide; a hydroxide; a sulfate; a hydrogen sulfate; a $(C_1-C_6)$alkyl sulfate, for instance a methyl sulfate or an ethyl sulfate; an acetate; a tartrate; an oxalate; a $(C_1-C_6)$alkylsulfonate such as methylsulfonate; an arylsulfonate that is unsubstituted or substituted with a $C_1-C_4$ alkyl radical, for instance a 4-tolylsulfonate. In at least one embodiment, $X^-$ is chosen from chloride and methyl sulfate.

According to at least one embodiment, in formula (V), $R_{17}$, $R_{18}$ and $R_{19}$, separately, may be chosen from $C_1-C_6$ alkyl radicals, $C_1-C_4$ monohydroxyalkyl radicals, $C_2-C_4$ polyhydroxyalkyl radicals, $(C_2-C_6)$alkoxy$(C_1C_4)$alkyl radicals, $C_2-C_6$ amidoalkyl radicals and tri$(C_1-C_6)$alkylsilane $(C_1-C_6)$alkyl radicals.

According to another embodiment, in formula (V), $R_{17}$ and $R_{18}$ together form a pyrrolidinium, piperidinium, homopiperidinium, piperazinium, homopiperazinium or morpholinium ring, and $R_{19}$ is then chosen from a $C_1-C_6$ alkyl radical; a $C_1-C_6$ monohydroxyalkyl radical; a $C_2-C_6$ polyhydroxyalkyl radical; a $C_2-C_6$ aminoalkyl radical; an aminoalkyl radical mono- or disubstituted with a $(C_1-C_6)$ alkyl radical and/or a $(C_1-C_6)$alkylcarbonyl radical; a $C_2-C_6$ carbamylalkyl radical; a tri$(C_1-C_6)$alkylsilane$(C_1-C_6)$alkyl radical; a $(C_1-C_6)$alkylcarboxy$(C_1-C_6)$alkyl radical; a $(C_1-C_6)$alkylcarbonyl$(C_2-C_6)$alkyl radical; and an N—$(C_1-C_6)$ alkylcarbamyl$(C_2-C_6)$alkyl radical.

According to one embodiment, $R_{17}$, $R_{18}$ and $R_{19}$ are alkyl radicals.

In one embodiment, in formula (V), D is a $C_1-C_6$ alkylene chain that may be substituted.

The cationic radical -D-Z may also be represented by formula (VI)

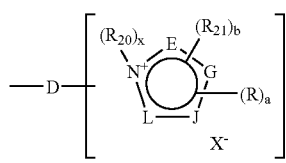

(VI)

in which

D is as defined above, the ring members E, G, J and L, which may be identical or different, represent atoms chosen from carbon, oxygen, sulfur and nitrogen atom to form pyrazolium, imidazolium, triazolium, oxazolium, isoxazolium, thiazolium or isothiazolium rings, a is an integer ranging from 1 to 3;

b is 0 or 1;

R, which may be identical or different, is chosen from hydrogen and halogen atoms, $C_1-C_6$ alkyl radicals, $C_1-C_6$ monohydroxyalkyl radicals, $C_2-C_6$ polyhydroxyalkyl radicals, $C_1-C_6$ alkoxy radicals, tri$(C_1-C_6)$ alkylsilane$(C_1-C_6)$alkyl radicals, amido radicals, carboxyl radicals, $C_1-C_6$ alkylcarbonyl radicals, $C_1-C_6$ thioalkyl radicals, $(C_1-C_6)$alkylthio radicals, amino radical disubstituted with at least one radical chosen from $(C_1-C_6)$alkyl, $(C_1-C_6)$alkylcarbonyl and $(C_1-C_6)$ alkylsulfonyl radicals, benzyl radicals, phenyl radicals optionally substituted with at least one radical chosen from methyl, hydroxyl, amino and methoxy radicals; with the proviso that the radicals R are borne by a carbon atom, $R_{21}$ is chosen from a $C_1-C_6$ alkyl radical, a $C_1-C_6$ monohydroxyalkyl radical, a trialkyl$(C_1-C_6)$silane $C_1-C_6$alkyl radical, a $C_2-C_6$ polyhydroxyalkyl radical, a $(C_1-C_6)$alkoxy$(C_1-C_6)$alkyl radical, a $C_2-C_6$ carbamylalkyl radical, a $(C_1-C_6)$alkylcarboxy$(C_1-C_6)$alkyl radical or a benzyl radical; with the proviso that the radical $R_{21}$ is borne by a nitrogen atom, $R_{20}$ is chosen from a $C_1-C_6$ alkyl radical; a $C_1-C_6$ monohydroxyalkyl radical; a $C_2-C_6$ polyhydroxyalkyl radical; a benzyl radical; a $(C_1-C_6)$aminoalkyl radical; a $(C_1-C_6)$aminoalkyl radical in which the amine is mono- or disubstituted with a $(C_1-C_6)$alkyl, $(C_1-C_6)$alkylcarbonyl, acylamino or $(C_1-C_6)$alkylsulfonyl radical; a carboxy$(C_1-C_6)$alkyl radical; a carbamyl$(C_1-C_6)$alkyl radical; a $(C_2-C_6)$trifluoroalkyl radical; a tri$(C_1-C_6)$ alkylsilane$(C_1-C_6)$alkyl radical; a sulfonamido$(C_2-C_6)$ alkyl radical; a $(C_1-C_6)$alkylcarboxy$(C_1-C_6)$alkyl radical; a $(C_1-C_6)$alkylsulfinyl$(C_2-C_6)$alkyl radical; a $(C_1-C_6)$alkylsulfonyl$(C_2-C_6)$alkyl radical; a $(C_1-C_6)$ alkylcarbonyl$(C_2-C_6)$alkyl radical; an N—$(C_1-C_6)$ alkylcarbamyl$(C_2-C_6)$alkyl radical; and an N—$(C_1-C_6)$ alkylsulfonamido$(C_2-C_6)$alkyl radical;

x is equal to 0 or 1, when x=0, the linker arm D is attached to the ammonium atom, when x=1, the linker arm D is attached to one of the ring members E, G, J or L, $X^-$ is a counterion as defined above.

In at least one embodiment, the ring members E, G, J and L form an imidazolium, pyrazolium, oxazolium, thiazolium or triazolium ring.

According to one embodiment of formula (VI), x is equal to 0 and D is a $C_1-C_4$ alkylene chain that may be substituted.

The cationic radical -D-Z may also be represented by formula (VII)

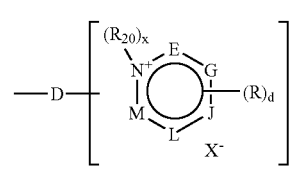

(VII)

in which

D, R and $R_{20}$ are as defined above, the ring members E, G, J, L and M, which may be identical or different, are chosen from carbon and nitrogen atoms and form a ring chosen from pyridinium, pyrimidinium, pyrazinium and pyridazinium rings, d is an integer ranging from 1 to 5, x is equal to 0 or 1, when x=0, the linker arm D is attached to the ammonium atom, when x=1, the linker arm D is attached to one of the ring members E, G, J, L or M, $X^-$ is a counterion as defined above.

In at least one embodiment, the ring members E, G, J, L and M form, with the quaternized nitrogen of the ring, a ring chosen from pyridinium, pyrimidinium, pyrazinium and pyridazinium rings.

According to one embodiment of formula (VII), x is equal to 0 and R is chosen from a hydrogen atom, a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, a $C_1$-$C_6$ alkylcarbonyl radical, an amino radical disubstituted with a $(C_1$-$C_6)$alkyl, $(C_1$-$C_6)$alkylcarbonyl or $(C_1$-$C_6)$alkylsulfonyl radical; with the proviso that the radicals R are borne by a carbon atom.

According to another embodiment of formula (VII), x is equal to 1, $R_{20}$ is chosen from a $C_1$-$C_6$ alkyl radical; a $C_1$-$C_6$ monohydroxyalkyl radical; a $C_2$-$C_6$ polyhydroxyalkyl radical; a $C_2$-$C_6$ aminoalkyl radical, a $C_2$-$C_6$ aminoalkyl radical in which the amine is mono- or disubstituted with at least one radical chosen from $(C_1$-$C_6)$alkyl, $(C_1$-$C_6)$alkylcarbonyl, acylamino and $(C_1$-$C_6)$alkylsulfonyl radicals; a $C_1$-$C_6$ carbamylalkyl radical; a $(C_1$-$C_6)$alkylcarbonyl$(C_1$-$C_6)$alkyl radical; an N—$(C_1$-$C_6)$alkylcarbamyl$(C_1$-$C_6)$alkyl radical; R is chosen from a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, a $C_1$-$C_6$ alkylcarbonyl radical, an amino radical disubstituted with at least one radical chosen from $(C_1$-$C_6)$alkyl, $(C_1$-$C_6)$alkylcarbonyl and $(C_1$-$C_6)$alkylsulfonyl radicals.

In one embodiment, $R_{20}$ is a $C_1$-$C_4$ alkyl radical that may be substituted with a hydroxyl or methoxy radical, and R is a hydrogen radical or a $C_1$-$C_4$ alkyl radical that may be optionally substituted with a hydroxyl or methoxy radical.

In formula (I), $W_1$ may, for example, be chosen from 5-aminopyrazole, 5-hydroxypyrazole, pyrazolo[1,5-a]pyridine, pyrazolo[1,5-a]pyrimidine, triaminopyrimidine and 2,3-diamino-6-alkoxypyridine radicals.

When $W_1$ is chosen from 5-aminopyrazole and 5-hydroxypyrazole radicals of formula (RI), then $R_7$ and $R_{11}$ are chosen independently from a hydrogen atom; linear or branched $C_1$-$C_4$ hydrocarbon-based chains that can form at least one 5- or 6-membered carbon-based ring and that may be saturated or unsaturated, wherein the carbon atoms may be, independently of each other, substituted with at least one halogen atom and/or with at keast one radical chosen from hydroxyl and amino radicals; $C_1$-$C_2$ alkoxy radicals; amino radicals; and (di)$(C_1$-$C_4)$alkylamino radicals.

According to another embodiment, $W_1$ is a radical of formula (RIII):

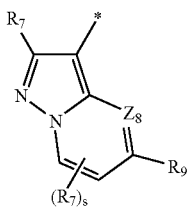

(RIII)

$R_7$, $R_8$ and $R_9$ being as defined above.

In this case, when $Z_8$ represents $CR_{12}$, then $R_7$, $R_9$ and $R_{12}$, which may be identical or different, may, for example, be chosen from:
a hydrogen atom,
amino radicals,
linear or branched $C_1$-$C_8$ hydrocarbon-based chains, which may form at least one 5- to 8-membered carbon-based ring, and which may be saturated or unsaturated, wherein at least one carbon atom of the carbon-based chain may be replaced with at least one entity chosen from oxygen, nitrogen and sulfur atom and $SO_2$ groups, and wherein the carbon atoms may be, independently of each other, substituted with at least one halogen atom; the radicals not comprising a peroxide bond or diazo or nitroso radicals, and not being linked directly to the nitrogen atom via an oxygen, sulfur or nitrogen atom.

In this embodiment, the radicals $R_7$, $R_9$ and $R_{12}$ may be chosen from a hydrogen atom; amino radicals; linear or branched $C_1$-$C_4$ hydrocarbon-based chains that may be saturated or unsaturated, wherein the carbon atoms may be, independently of each other, substituted with at least one halogen atom and/or with at least one radical chosen from hydroxyl and amino radicals; $C_1$-$C_2$ alkoxy radicals; amino radicals; and optionally substituted (di)$(C_1$-$C_4)$alkylamino radicals.

In formula (RIII), when $Z_8$ represents N, then $R_7$ and $R_9$ are chosen from a hydrogen atom; linear or branched $C_1$-$C_6$ alkyl radicals; $C_1$-$C_6$ monohydroxyalkyl radicals; $C_2$-$C_6$ polyhydroxyalkyl radicals; $C_1$-$C_6$ aminoalkyl radicals, $C_1$-$C_6$ aminoalkyl radicals in which the amine is mono- or disubstituted with at least one radical chosen from $(C_1$-$C_6)$ alkyl and $(C_1$-$C_6)$alkylcarbonyl radicals; hydroxyl and amino radicals, the amino possibly being substituted with at least one linear or branched $C_1$-$C_{10}$ alkyl radical, which can form at least one 5- to 6-membered carbon-based ring, and which may be saturated or unsaturated, wherein the carbon atoms may be, independently of each other, substituted with at least one halogen atom and/or with at least one radical chosen from hydroxyl and amino radicals; $C_1$-$C_2$ alkoxy radicals.

According to one embodiment, $W_1$ is a pyrazolo[1,5-a]pyridine or pyrazolo[1,5-a]pyrimidine derivative in which $R_7$, $R_9$ and $R_{12}$ are chosen from hydrogen, $C_1$-$C_4$ alkyl radicals, amino radicals, $C_1$-$C_4$ monoalkylamino radicals; $C_1$-$C_4$ dialkylamino radicals, $C_1$-$C_4$ hydroxyalkyl radicals; and $C_1$-$C_4$ alkoxy radicals.

By way of example, the following compounds of formula (I) may be mentioned, but are not limited to:

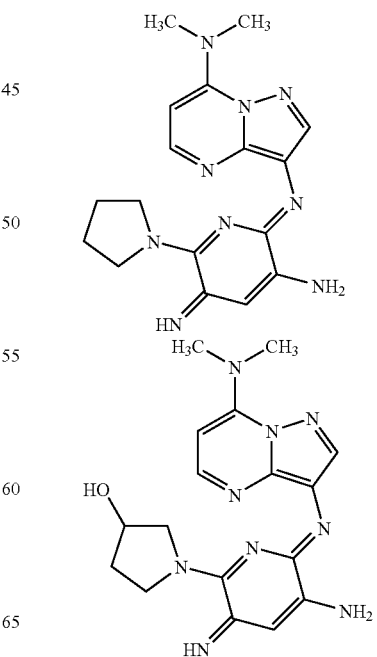

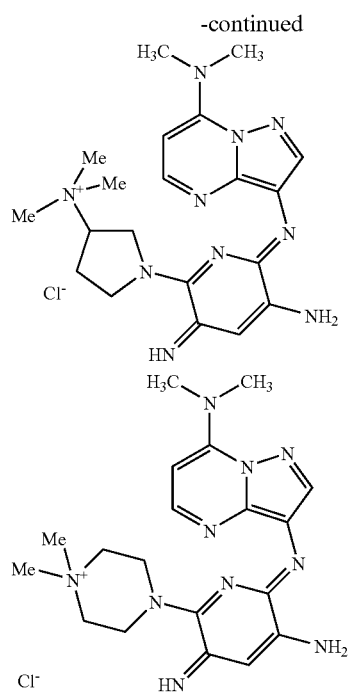
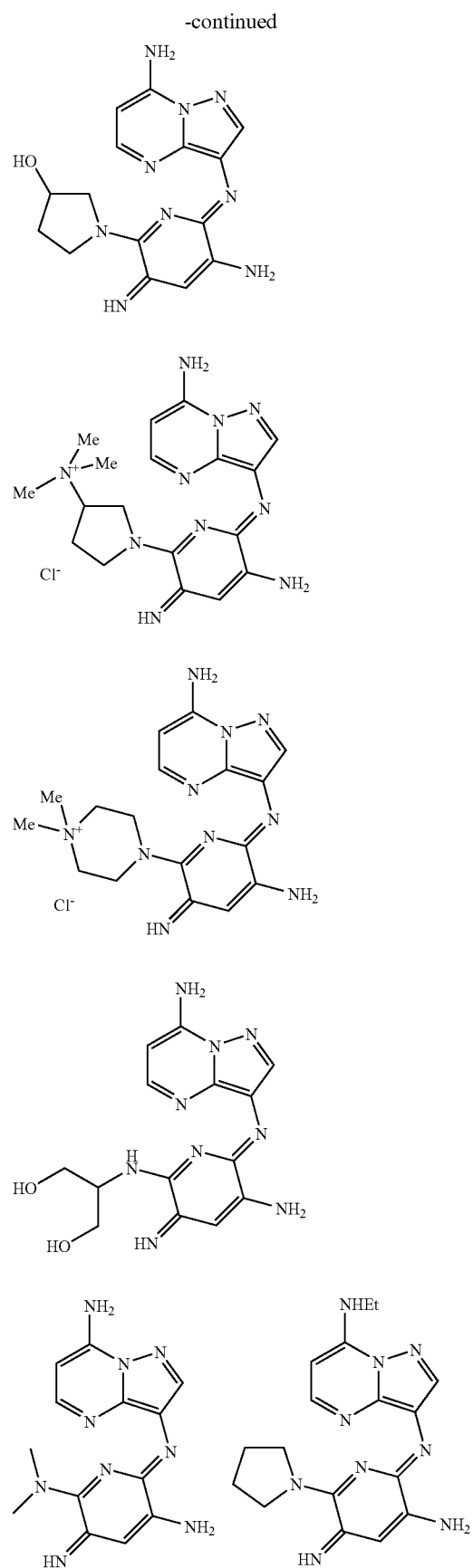

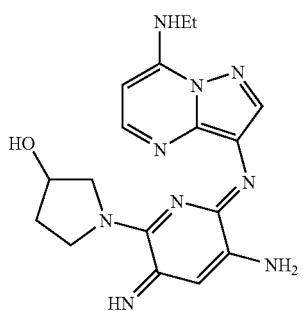
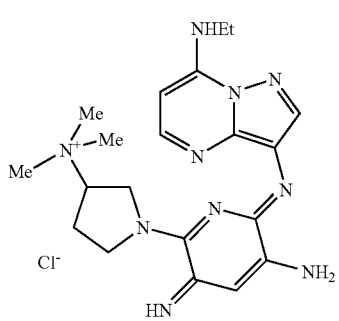
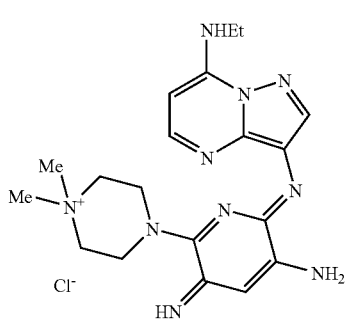
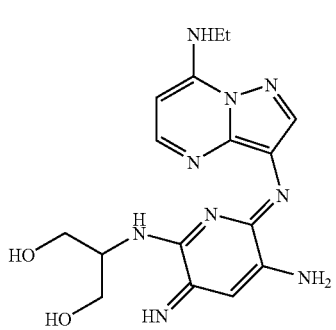
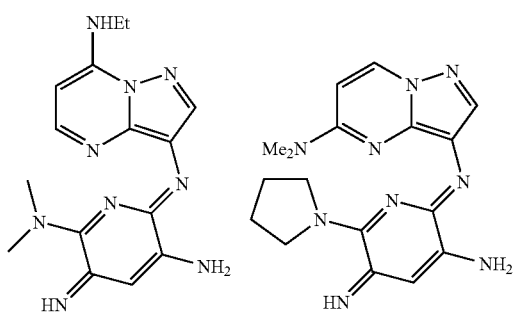
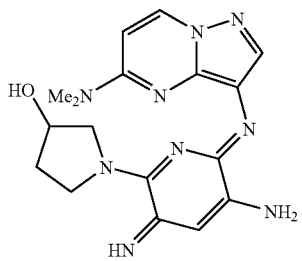
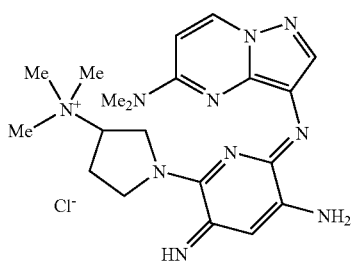
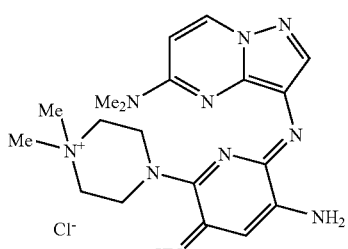
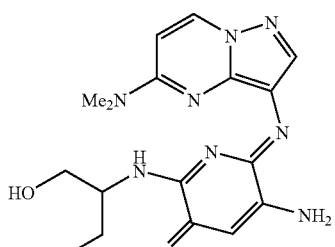
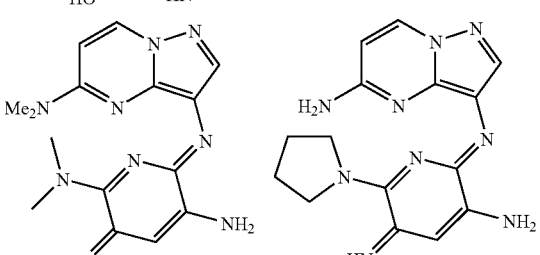
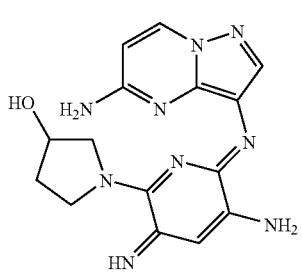

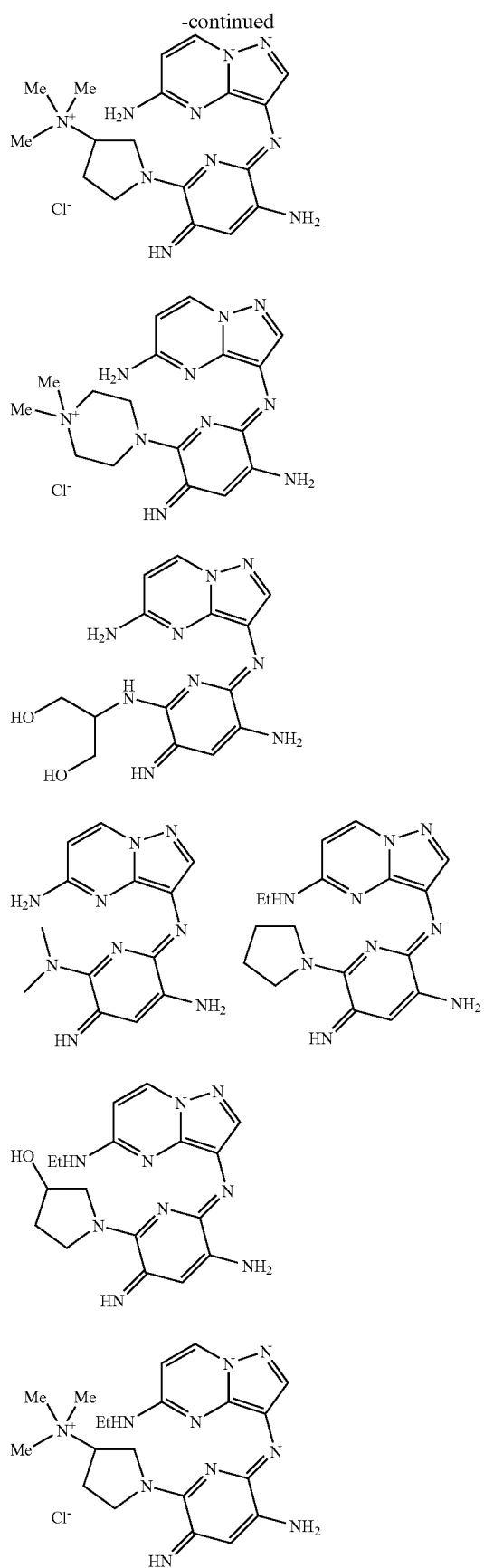
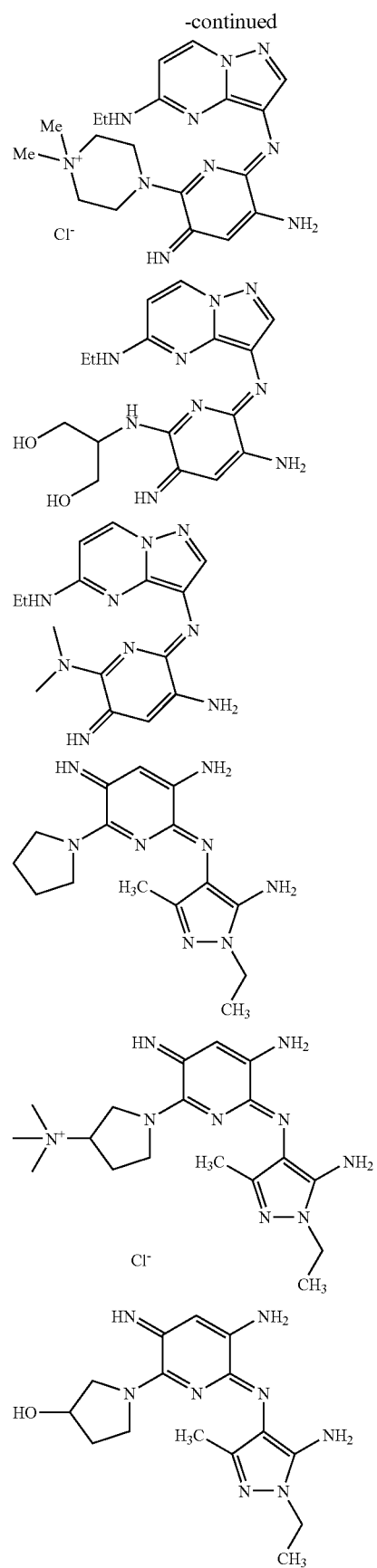

-continued
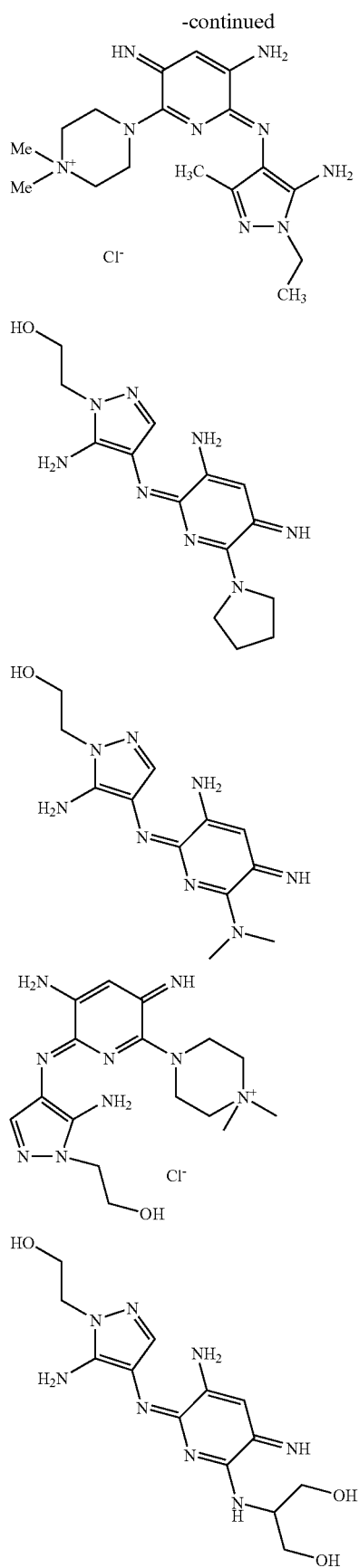
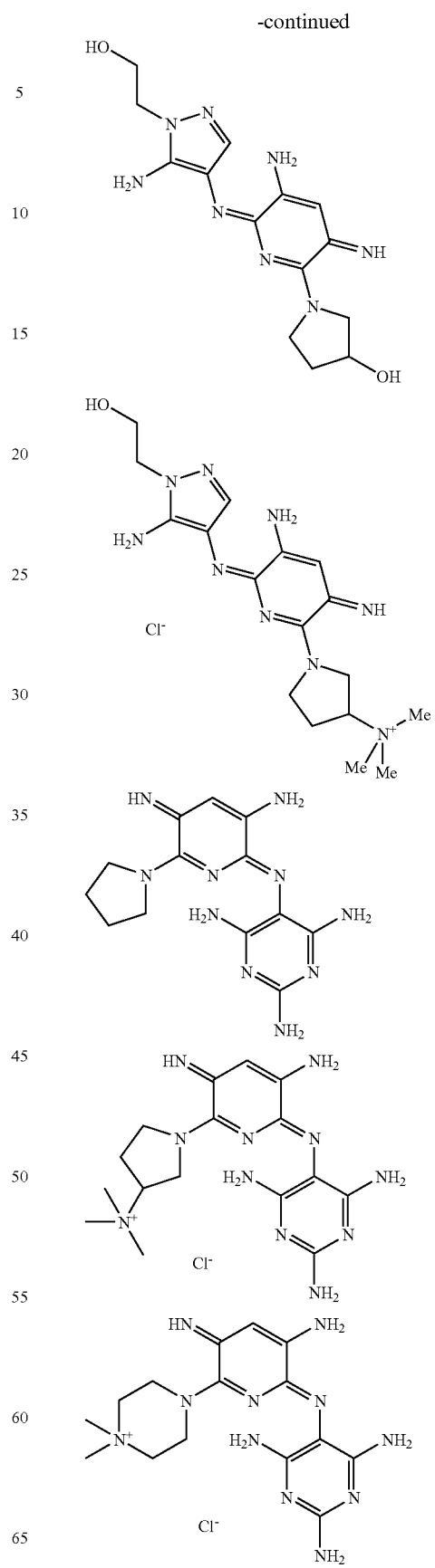

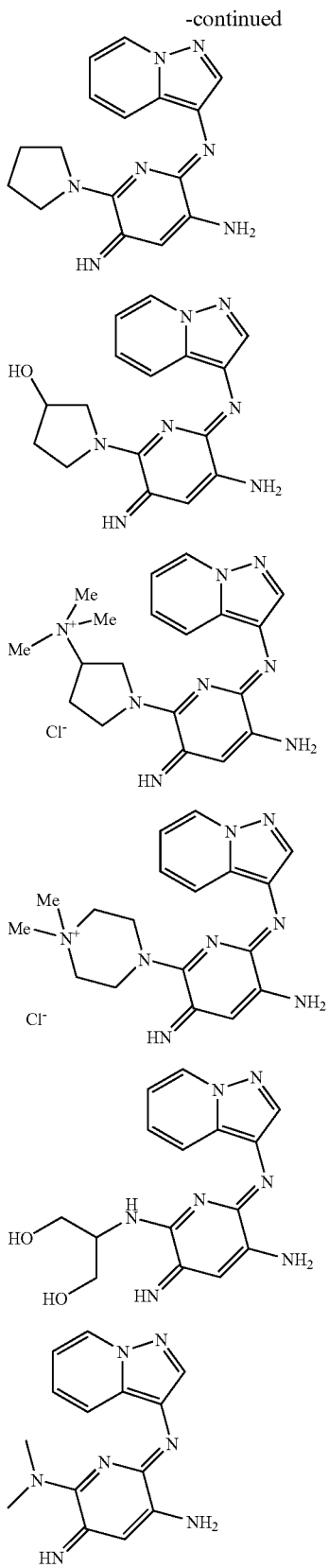

According to one embodiment, the compound of formula (I) may be represented by one of the following formulae:

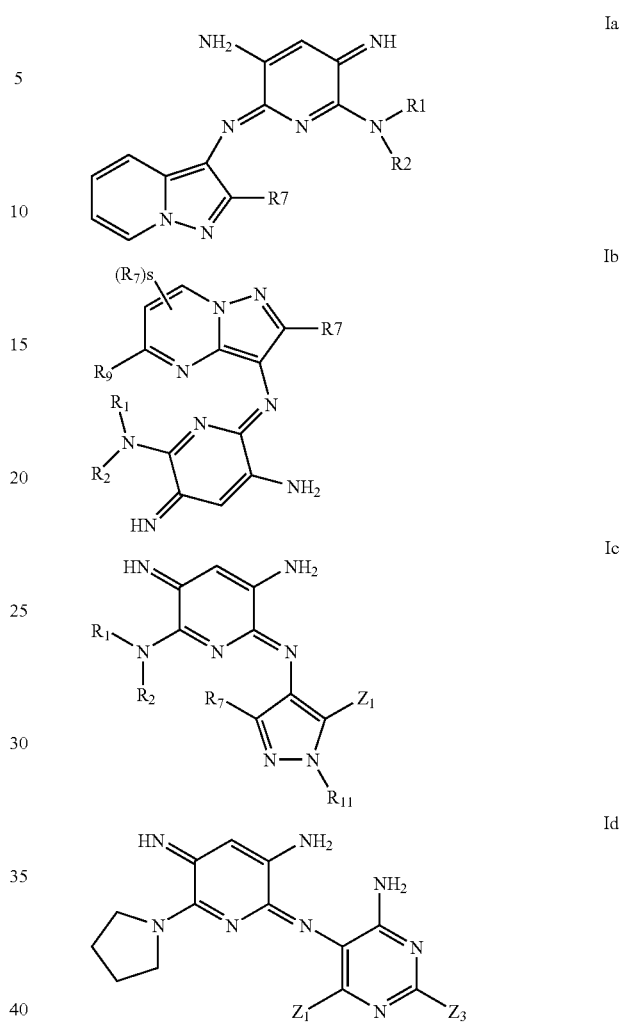

in which $R_1$, $R_2$, $R_6$, $R_7$, $R_8$, $R_9$, $R_{11}$, $Z_1$, $Z_2$ and $Z_3$ are as defined above.

The composition disclosed herein may contain an amount of compound (I) ranging from 0.005% to 10% by weight relative to the total weight of the composition. For example, compound (I) may be present in an amount ranging from 0.01% to 10% by weight, such as from 0.1% to 5% by weight.

The dye composition in accordance with the present disclosure may also contain at least one additional direct dye other than the compounds of formula (I). These direct dyes that are useful according to the disclosure are chosen, for example, from neutral, acidic or cationic nitrobenzene direct dyes, neutral, acidic or cationic azo direct dyes, quinone direct dyes, such as neutral, acidic or cationic anthraquinone direct dyes, azine direct dyes, triarylmethane direct dyes, indoamine direct dyes, direct dyes of tetraazapentamethine type and natural direct dyes.

Among the benzene-based direct dyes that may be used according to the present disclosure, mention may be made, in a non-limiting manner, of the following compounds:

1,4-diamino-2-nitrobenzene
1-amino-2-nitro-4-β-hydroxyethylaminobenzene
1-amino-2-nitro-4-bis(β-hydroxyethyl)aminobenzene 1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo direct dyes that may be used according to the present disclosure, non-limiting mention may be made of the cationic azo dyes described in patent applications WO 95/15144, WO-95/01772 and EP-714 954, the content of which forms an integral part of the invention.

Among these compounds that may be mentioned, for example, are the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned, for example, are the following dyes, described in the Color Index International 3rd edition:
Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Non-limiting mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes that may be mentioned, for example, are the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
1-N-Methylmorpholiniumpropylamino-4-hydroxyanthraquinone
1-Aminopropylamino-4-methylaminoanthraquinone
1-Aminopropylaminoanthraquinone
5-β-Hydroxyethyl-1,4-diaminoanthraquinone
2-Aminoethylaminoanthraquinone
1,4-Bis(β,γ-dihydroxypropylamino)anthraquinone.

Among the azine dyes that may be mentioned, for example, are the following compounds:
Basic Blue 17
Basic Red 2.

Among the triarylmethane dyes, non-limiting mention may be made of the following compounds: Basic. Green 1, Acid Blue 9, Basic Violet 3, Basic Violet 14, Basic Blue 7, Acid Violet 49, Basic Blue 26, Acid Blue 7.

Among the indoamine dyes, non-limiting mention may be made of the following compounds:
2-β-Hydroxyethylamino-5-[bis(β-4'-hydroxyethyl)amino]anilino-1,4-benzoquinone
2-β-Hydroxyethylamino-5-(2'-methoxy-4'-amino)anilino-1,4-benzoquinone
3-N-(2'-Chloro-4'-hydroxy)phenylacetylamino-6-methoxy-1,4-benzoquinone imine
3-N-(3'-Chloro-4'-methylamino)phenylureido-6-methyl-1,4-benzoquinone imine
3-[4'-N-(Ethyl,carbamylmethyl)amino]phenylureido-6-methyl-1,4-benzoquinone imine.

Among the dyes of the tetraazapentamethine type that may be used according to the present disclosure, non-limiting mention may be made of the compounds given in the table below, An representing an organic or mineral anion chosen, for example, from a halide such as chloride, bromide, fluoride or iodide; a hydroxide; a sulfate; a hydrogen sulfate; a $(C_1-C_6)$alkyl sulfate, for instance a methyl sulfate or an ethyl sulfate; an acetate; a tartrate; an oxalate; a $(C_1-C_6)$alkylsulfonate such as methylsulfonate; an arylsulfonate that is unsubstituted or substituted with a $C_1-C_4$ alkyl radical, for instance a 4-tolylsulfonate. IN at least one embodiment, An is a chloride or a methyl sulfate.

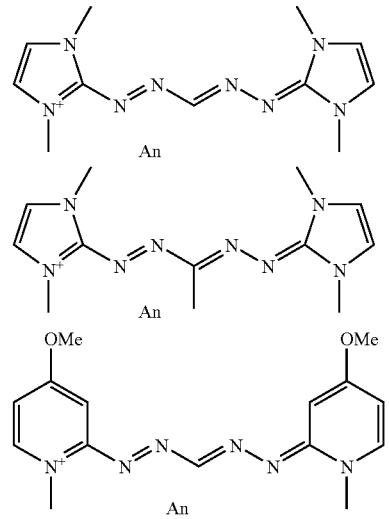

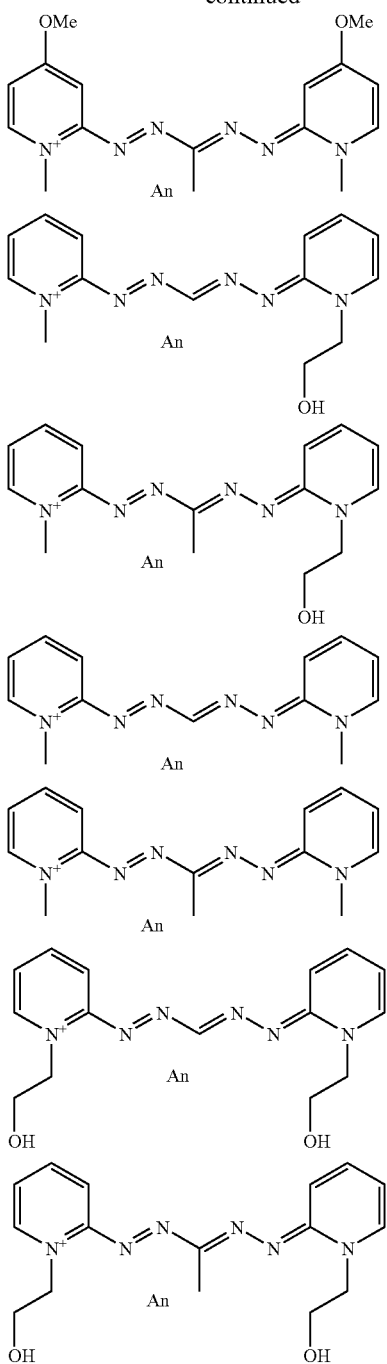

Among the natural direct dyes that may be used according to the present disclosure, non-limiting mention may be made of lawsone, juglone, alizarin; purpurin, carminic acid, kermesic acid, purpurogallin, protocatechaldehyde, indigo, isatin, curcumin, spinulosin and apigenidin. It is also possible to use extracts or decoctions containing these natural dyes, such as henna-based poultices or extracts.

The at least one additional direct dye may be present in the composition in an amount ranging from 0.001% to 20% by weight relative to the total weight of the ready-to-use composition, such as from 0.005% to 10% by weight.

The composition of the present disclosure may also contain oxidation bases and couplers conventionally used for oxidation dyeing.

Non-limiting examples that may be mentioned include para-phenylenediamines, bis(phenyl)alkylenediamines, para-aminophenols, ortho-aminophenols and heterocyclic bases, and the addition salts thereof.

The couplers are, for example, meta-phenylenediamine couplers, meta-aminophenol couplers, meta-diphenol couplers, naphthalene-based couplers and heterocyclic couplers, and the addition salts thereof.

When they are present, the bases and couplers may each be present in an amount ranging from 0.001% to 10% by weight, such as from 0.005% to 6% by weight relative to the total weight of the dye composition.

The medium that is suitable for dyeing, also known as the dye support, comprises water or a mixture of water and of at least one organic solvent to dissolve the compounds that would not be sufficiently water-soluble. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

For dyeing human keratin fibers, the dyeing medium is a suitable cosmetic medium.

The solvents may be present in an amount ranging from 1% to 40% by weight, such as from 5% to 30% by weight relative to the total weight of the dye composition.

The dye composition in accordance with the present disclosure may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, such as anionic, cationic, nonionic and amphoteric polymeric associative thickeners, antioxidants, penetrating agents, sequestering agents, fragrances, buffers, dispersants, conditioners, for instance volatile or non-volatile, modified or unmodified silicones, film-forming agents, ceramides, preserving agents and opacifiers.

The above adjuvants may be present in an amount for each one ranging from 0.01% to 20% by weight relative to the weight of the composition.

Needless to say, a person skilled in the art will take care to select this or these optional additional compound(s) such that the advantageous properties intrinsically associated with the oxidation dye composition in accordance with the present disclosure are not, or are not substantially, adversely affected by the envisaged addition(s).

The pH of the dye composition in accordance with the present disclosure ranges from 3 to 12, such as from 5 to 11. It may be adjusted to the desired value by means of acidifying or basifying agents usually used in the dyeing of keratin fibers or by using standard buffer systems.

Among the acidifying agents that may be mentioned, for example, are mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents that may be mentioned, for example, are aqueous ammonia, alkali metal carbonates, alkanolamines such as mono-, di- or triethanolamine and also derivatives thereof, sodium hydroxide, potassium hydroxide and the compounds of the following formula:

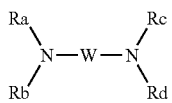

in which W is a propylene residue optionally substituted with a hydroxyl group or with a $C_1$-$C_4$ alkyl radical; $R_a$, $R_b$, $R_c$ and $R_d$, which may be identical or different, are chosen from a hydrogen atom, $C_1$-$C_4$ alkyl radicals, and $C_1$-$C_4$ hydroxyalkyl radicals.

The dye composition according to the present disclosure may be in various forms, such as in the form of liquids, creams or gels, or in any other form that it suitable for dyeing keratin fibers, such as human hair.

The present disclosure also relates to a process of direct dyeing which comprises the application of a dye composition, containing a dye of formula (I) as defined above, to keratin fibers. After an action time, the keratin fibers are rinsed, allowing the colored fibers to show. The action time may range from 3 to 50 minutes, such as from 5 to 30 minutes.

When the dye composition comprises an oxidation base and/or a coupler, the dye composition may then contain an oxidizing agent. The oxidizing agents conventionally used for the oxidation dyeing of keratin fibers are, for example, hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. In at least one embodiment, hydrogen peroxide is used.

The oxidizing agent may be added to the composition just at the time of use, or it may be used starting with an oxidizing composition containing it, which is applied simultaneously or sequentially to the composition disclosed herein. The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibers may range from 3 to 12, such as from 5 to 11. The pH may be adjusted to the desired value using acidifying or basifying agents usually used in the dyeing of keratin fibers and as defined above.

The composition that is finally applied to the keratin fibers may be in various forms, such as in the form of liquids, creams or gels or in any other form that is suitable for dyeing keratin fibers, such as human hair.

In at least one embodiment, the compounds of formula (I) are prepared by mixing a compound of formulae (RI') to (RVIII') and a compound of formula (VIII) in the presence of an oxidizing agent, these compounds being as defined below.

(RI')

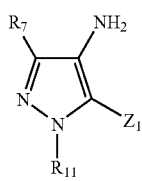

(RII')

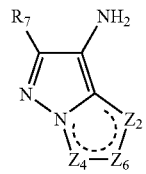

(RIII')

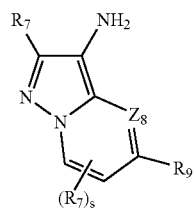

(RIV')

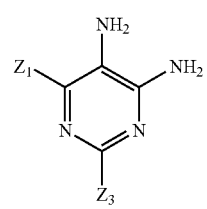

(RV')

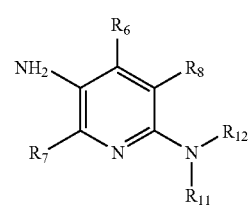

(RVI')

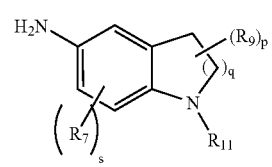

(RVII')

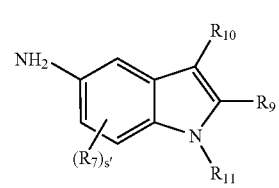

(RVIII')

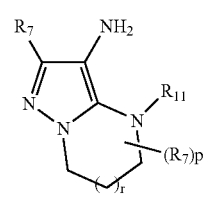

In these formulae, the radicals are as defined above for formulae RI, RII, RIII, RIV, RV, RVI, RVII and RVIII.

The compound of formula (VIII) is represented by

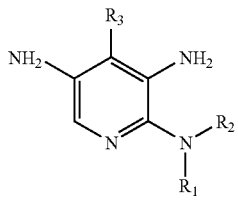
(VIII)

in which $R_1$, $R_2$ and $R_3$ have the same meanings as above.

According to one embodiment, a compound of formulae (RI') to (RVIII') is mixed with a compound of formula (VIII) in a solvent with a boiling point ranging from 60° C. to 180° C., such as from 60° C. to 110° C., for example acetonitrile, or an alcohol such as methanol or ethanol or a mixture thereof with water. To the reaction medium is added, at a temperature of from 0° C. to 10° C., a mineral or organic base, for example sodium hydroxide, potassium hydroxide or a trialkylamine, the pH being adjusted to 4 to 12, such as from 7 to 9; next, an organic or mineral oxidizing agent, for example aqueous hydrogen peroxide solution, cerium (IV) ammonium nitrate (CAN), silver oxide or a peracid such as meta-perbenzoic acid, performic acid or peracetic acid, is added to the medium. Once the reagents have been consumed, water is added to the reaction medium and the organic and aqueous phases are separated by the standard methods. The aqueous phase is then extracted several times with butanol, dried over sodium or magnesium sulfate and then distilled until a crude reaction product is obtained in the form of a powder or an oil. This residue is purified by recrystallization, optionally fractional recrystallization, and/or by chromatography on silica $SiO_2$.

The compounds of formulae (RI') to (RVIII') are compounds that are well known in the art. For example, the compounds of formula RI' may be obtained according to the synthetic processes described in patent applications FR 2 733 749, FR 2 827 601 and DE 19 619 112. The compounds of formula RII' may be obtained according to the synthetic processes described in patent application EP 923 929. The compounds of formula RIII' may be obtained according to the synthetic processes described in patent applications EP 926 149 and FR 2 771 631. The compounds of formula RIV' may be obtained according to the synthetic processes described in patent applications DE 2 613 707, DE 2 554 456 and DE 2 516 117. The compounds of formula RV' may be obtained according to the synthetic processes described in patent application FR 2 832 148. The compounds of formula RVI' may be obtained according to the synthetic processes described in patent application JP 11 158 047. The compounds of formula RVII' may be obtained according to the synthetic processes described in patent application EP 424 261. The compounds of formula RVIII' may be obtained according to the synthetic processes described in patent applications EP 728 464 and EP 740 931, and DE 4 133 957.

The compounds of formula VIII may be obtained according to the synthetic processes described in patent application FR 1 397 551. Some of these compounds may also be synthesized according to the following synthetic scheme:

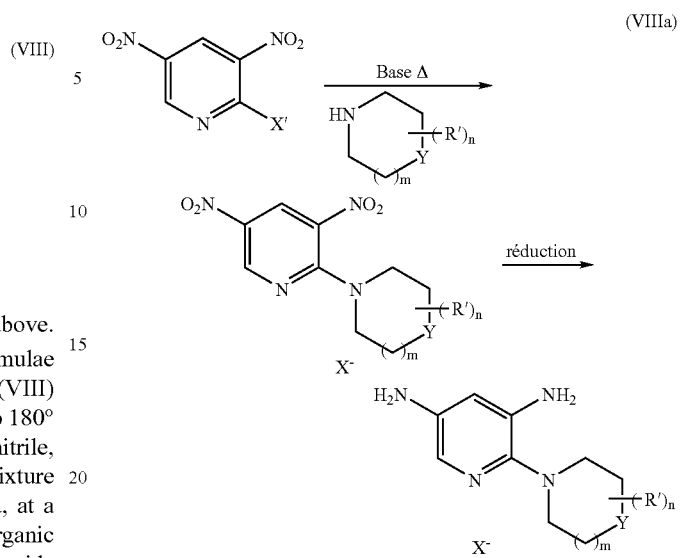
(VIIIa)

wherein X' is chosen from a halogen atom such as a chlorine or bromine atom, and from a $C_1$-$C_2$ alkoxy radical, and R', Y, $X^-$, n and m are as defined above.

The nitro compounds may be obtained in general by dissolving, with stirring, a 2-halo-3,5-dinitropyridine or 2-alkoxy-3,5-dinitropyridine such as 2-chloro-3,5-dinitropyridine or 2-methoxy-3,4-dinitropyridine in a protic or aprotic solvent with a boiling point of from 40° C. to 180° C., for instance dichloromethane, dioxane, DMF, THF, a lower alcohol or water, and in the presence of an organic or mineral base that can form a salt with the ion released. The cyclic amine is then introduced dropwise. The temperature of the reaction medium is generally from 25° C. to 100° C. After the reagents have disappeared, the reaction medium is cooled to room temperature and poured onto a mixture of ice and water. The precipitate thus formed is filtered off by suction on a sinter funnel, washed with water and then dried under vacuum to constant weight.

The compounds of formula (VIIIa) may then be obtained by reducing the nitro precursors, either by catalytic hydrogenation or by hydrogen transfer, either with a metal such as zinc, tin or iron, or with a hydride such as sodium borohydride or lithium aluminium hydride. The reaction used is, in at least one embodiment, heterogeneous catalytic hydrogenation or phase transfer with cyclohexene. The solvent is a protic or aprotic solvent, such as dichloromethane or an alcohol with a boiling point of from 66° C. to 160° C. The catalyst is conventionally palladium-on-charcoal. The hydrogenation reaction is generally performed at a temperature of from 25° C. to 80° C. under a hydrogen pressure of between 1 bar and 40 bar, such as from 1 bar to 6 bar.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements. The examples that follow serve to illustrate the invention without, however, being limiting in nature.

EXAMPLES

Example 1

Preparation of Compound 3

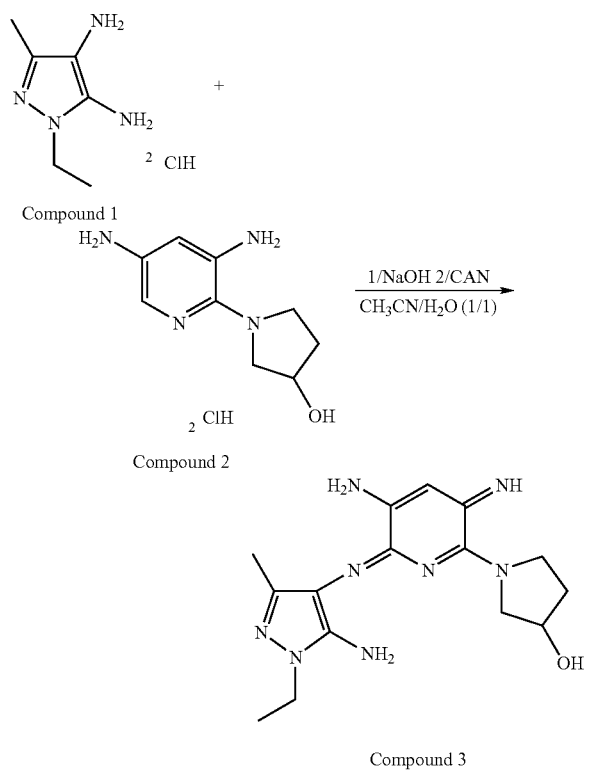

Into a mixture of 10 ml of acetonitrile and 10 ml of water, with stirring and at room temperature, were introduced 109 mg (0.51 mmol; 1 eq.) of compound 1 and 100 mg (0.374 mmol; 1 eq.) of compound 2. 1 M sodium hydroxide was then added dropwise to keep the pH between 7 and 8, while 410 mg of cerium ammonium nitrate (CAN, 0.748 mmol; 2 eq.) dissolved in 10 ml of water were added. Within a few minutes, the solution turned green-black. The mixture was left to react for 2 hours. The aqueous phase was then extracted with butanol: the organic phase was dried over sodium sulfate and then evaporated under vacuum. The solution was evaporated to dryness and the residue obtained was then taken up in acetone (20 ml) and filtered again. 127.5 mg of a black powder (compound 3) having the characteristics below were thus obtained:

Mass (ESI ±): 331 (MH)$^+$, 329 (MH)$^-$.

$^1$H NMR (400 MHz, MeOD): 6.25 (s, 1H); 4.52 (s, 1H); 3.98 (m, 2H); 3.87 (q, 2H); 3.68 (m, 2H); 2.21 (s, 3H); 2.07 (m, 2H); 1.31 (t, 3H).

Absorbance (acetonitrile): $\lambda_{max}$=408 nm, $\lambda_{max}$=580 nm

Example 2

Preparation of Compound 6

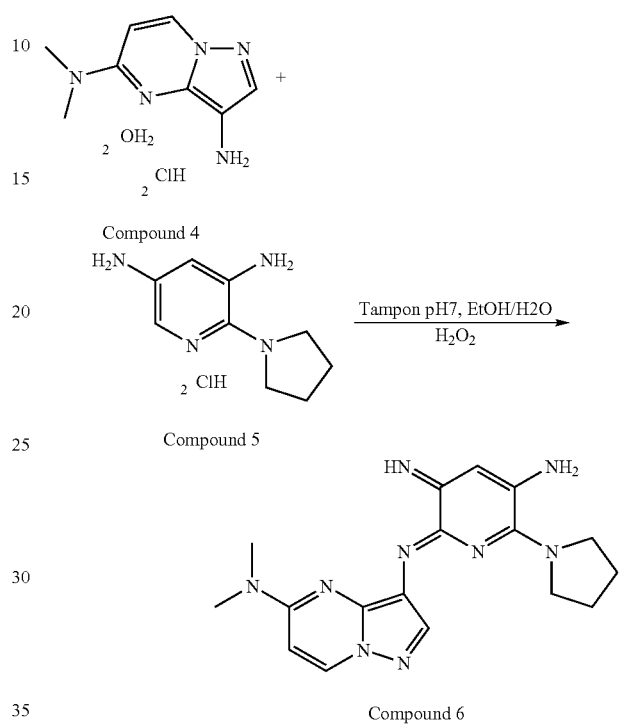

99.9 mg (0.349 mmol) of compound 4 and 99.6 mg (0.396 mmol) of compound 5 were dissolved in 10 ml of a mixture consisting of ethanol, water (30/70) and pH 7 buffer (respective proportions 4:1). After dissolution, 10 ml of 20-volumes aqueous hydrogen peroxide solution were added. The reaction medium turned black over one hour. The resulting medium was then freeze-dried. After purification by reverse-phase chromatography, evaporation of the elution solvents and drying, 85 mg of a black solid having the characteristics below were recovered:

Mass (ESI ±): 352 (MH)$^+$

Absorbance (acetonitrile): $\lambda$=447 nm, $\lambda$=583 nm.

Example 3

Preparation of Compound 8

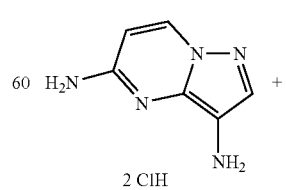

Compound 7

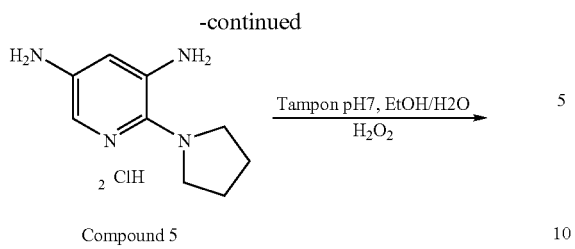

Compound 5

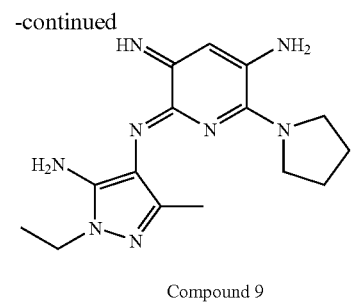

Compound 9

18 mg (0.081 mmol) of compound 7 and 20 mg (0.079 mmol) of compound 8 were dissolved in 2 ml of a mixture consisting of ethanol, water (30/70) and pH 7 buffer (respective proportions 4:1). After dissolution, 2 ml of 20-volumes aqueous hydrogen peroxide solution were added. The reaction medium turned black over 70 minutes. The resulting medium was then freeze-dried. After purification by reverse-phase chromatography, evaporation of the elution solvents and drying, 10 mg of a black solid having the characteristics below were recovered:

Mass (ESI ±): 324 (MH)$^+$ $^1$H NMR (400 MHz, CD$_3$OD): 2.05 (m, 4H); 3.90 ppm (m, 4H); 5.96 (s, 1H); 6.40 (d, 1H); 8.36 (d, 1H); 8.74 (s, 1H).

Absorbance (acetonitrile): λ=442 nm, λ=539 nm, λ=577 nm.

16.6 mg (0.078 mmol) of compound 1 and 20 mg (0.079 mmol) of compound 5 were dissolved in 2 ml of a mixture consisting of ethanol, water (30/70) and pH 7 buffer (respective proportions 4:1). After dissolution, 2 ml of 20-volumes aqueous hydrogen peroxide solution were added. The reaction medium turned black over 70 minutes. The resulting medium was then freeze-dried. After purification by reverse-phase chromatography, evaporation of the elution solvents and drying, 11 mg of a black solid having the characteristics below were recovered:

Mass (ESI ±): 315 (MH)$^+$ $^1$H NMR (400 MHz, CD$_3$OD): 1.32 ppm (t, 3H); 1.99 ppm (m, 4H); 2.19 ppm (s, 3H); 3.79 (m, 4H); 3.87 (q, 2H); 6 (s, 1H).

Absorbance (acetonitrile): λ=407 nm, λ=581 nm.

Example 5

Preparation of Compound 11

Example 4

Preparation of Compound 9

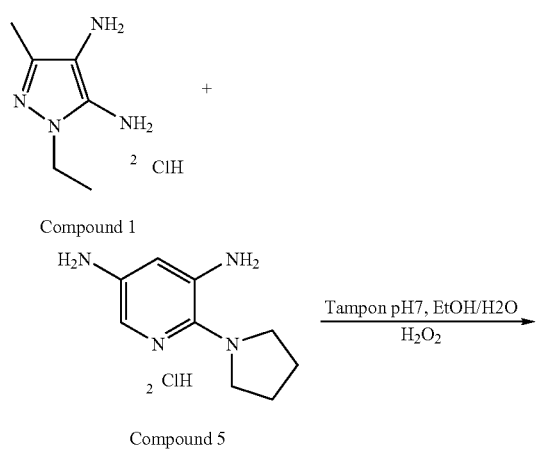

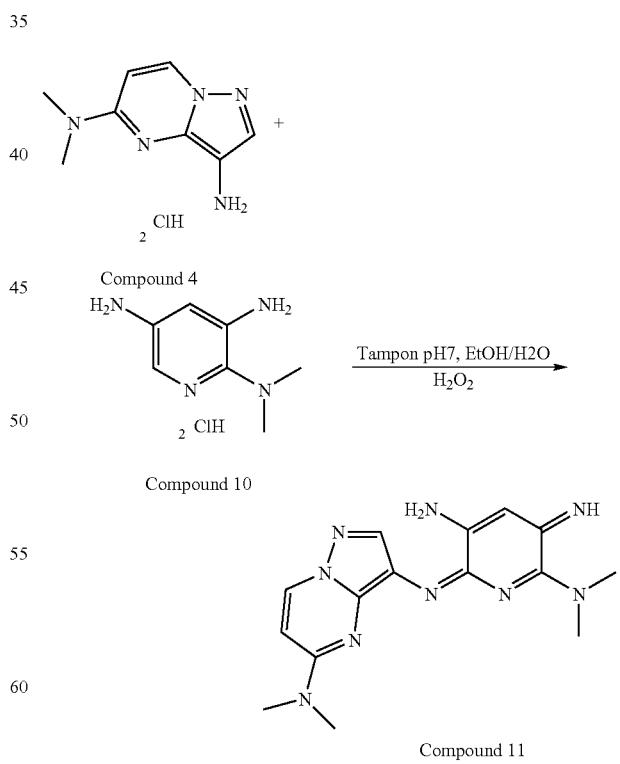

5 mg (0.02 mmol) of compound 4 and 4.5 mg (0.02 mmol) of compound 10 were dissolved in 0.5 ml of a mixture consisting of ethanol, water (30/70) and pH 7 buffer (respective proportions 4:1). After dissolution, 0.5 ml of 20-volumes aqueous hydrogen peroxide solution was added. The reaction medium turned black over one hour. The resulting medium was then freeze-dried. After purification by reverse-phase chromatography, evaporation of the elution solvents and drying, 3 mg of a black solid having the characteristics below were recovered:

Mass (ESI ±): 326 (MH)$^+$ $^1$H NMR (400 MHz, CD$_3$OD): 3.29 ppm (s, 12H); 5.96 ppm (s, 1H); 6.65 ppm (d, 1H); 8.39 ppm (d, 1H); 8.82 ppm (s, 1H).

Absorbance (acetonitrile): λ=457 nm, λ=578 nm.

Example 6

Preparation of Compound 13

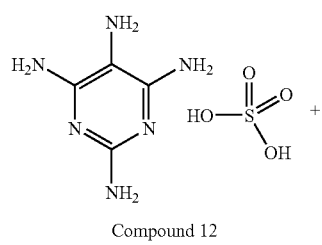

Compound 12

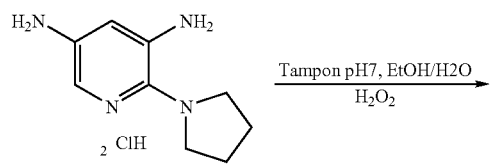

Compound 5

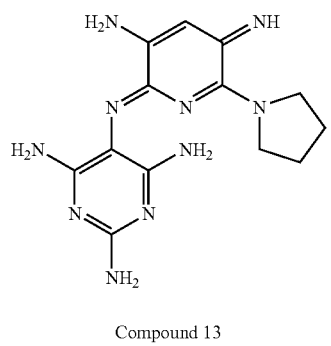

Compound 13

50 mg (0.21 mmol) of compound 12 and 48 mg (0.019 mmol) of compound 5 were dissolved in 5 ml of a mixture consisting of ethanol, water (30/70) and pH 7 buffer (respective proportions 4:1). After dissolution, 5 ml of 20-volumes aqueous hydrogen peroxide solution were added. The reaction medium turned black over 70 minutes. The resulting medium was then freeze-dried. After purification by reverse-phase chromatography, evaporation of the elution solvents and drying, 11 mg of a black solid having the characteristics below were recovered:

Mass (ESI ±): 315 (MH)$^+$ $^1$H NMR (400 MHz, CD$_3$OD): 2.01 ppm (m, 4H); 3.73 (m, 4H); 6.21 ppm (s, 1H).

Absorbance (acetonitrile): λ=435 nm, λ=607 nm.

Example 7

Preparation of Compound 15

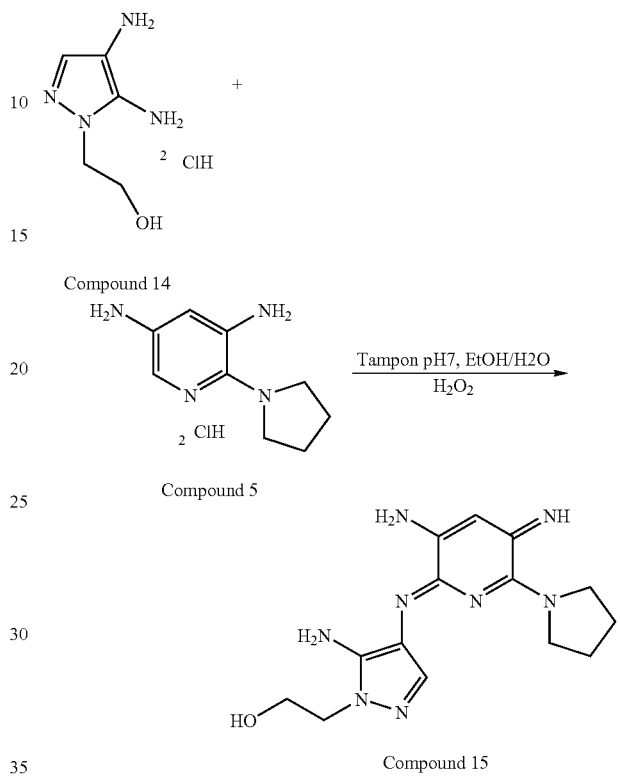

4.3 mg (0.02 mmol) of compound 14 and 5 mg (0.02 mmol) of compound 5 were dissolved in 0.5 ml of a mixture consisting of ethanol, water (30/70) and pH 7 buffer (respective proportions 4:1). After dissolution, 0.5 ml of 20-volumes aqueous hydrogen peroxide solution was added. The reaction medium turned black over one hour. The resulting medium was then freeze-dried. After purification by reverse-phase chromatography, evaporation of the elution solvents and drying, 3 mg of a black solid having the characteristics below were recovered:

Mass (ESI ±): 317 (MH)$^+$ $^1$H NMR (400 MHz, CD$_3$OD): 2.01 ppm (m, 4H); 3.86 ppm (m, 6H); 4.04 ppm (m, 2H); 5.91 ppm (s, 1H); 8.09 ppm (s, 1H).

Absorbance (acetonitrile): λ=438 nm, λ=571 nm.

Example 8

Preparation of Compound 17

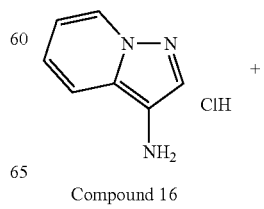

Compound 16

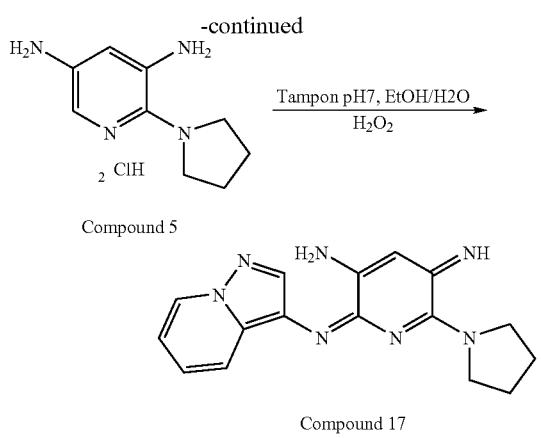

Compound 5

Compound 17

3.3 mg (0.02 mmol) of compound 16 and 5 mg (0.02 mmol) of compound 5 were dissolved in 0.5 ml of a mixture consisting of ethanol, water (30/70) and pH 7 buffer (respective proportions 4:1). After dissolution, 0.5 ml of 20-volumes aqueous hydrogen peroxide solution was added. The reaction medium turned black over one hour. The resulting medium was then freeze-dried. After purification by reverse-phase chromatography, evaporation of the elution solvents and drying, 3 mg of a black solid having the characteristics below were recovered:

Mass (ESI ±): 308 (MH)+

$^1$H NMR (400 MHz, CD$_3$OD): 2.07 ppm (m, 4H); 3.91 ppm (m, 4H); 6.06 ppm (s, 1H); 7 ppm (m, 1H); 7.37 ppm (m, 1H); 8.06 ppm (d, 1H); 8.49 ppm (d, 1H); 8.78 ppm (s, 1H).

Absorbance (acetonitrile): λ=448 nm, λ=575 nm.

Example 9

Preparation of Compound 19

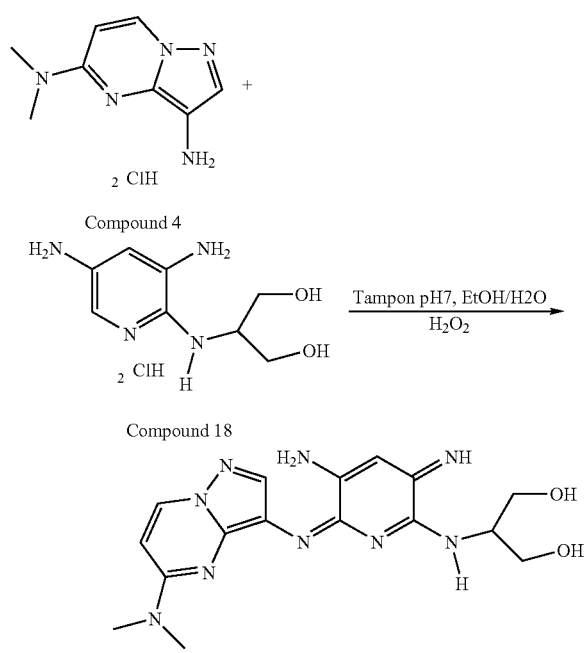

Compound 4

Compound 18

Compound 19

(0.02 mmol) of compound 4 and 5.4 mg (0.02 mmol) of compound 18 were dissolved in 0.5 ml of a mixture consisting of ethanol, water (30/70) and pH 7 buffer (respective proportions 4:1). After dissolution, 0.5 ml of 20-volumes aqueous hydrogen peroxide solution was added. The reaction medium turned black over one hour. The resulting medium was then freeze-dried. After purification by reverse-phase chromatography, evaporation of the elution solvents and drying, 3 mg of a black solid having the characteristics below were recovered:

Mass (ESI ±): 372 (MH)+

$^1$H NMR (400 MHz, CD$_3$OD): 3.31 ppm (s, 6H); 3.93-3.82 ppm (m, 4H); 4.43 ppm (m, 1H); 6.16 ppm (s, 1H); 6.68 ppm (d, 1H); 8.41 ppm (d, 1H); 8.85 ppm (s, 1H).

Absorbance (acetonitrile): λ=451 nm, λ=575 nm.

Example 10

Preparation of Compound 21

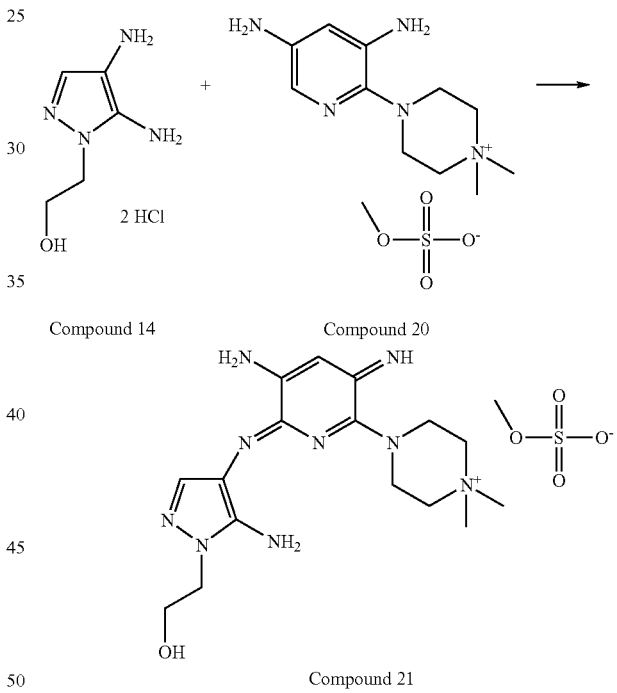

Compound 14        Compound 20

Compound 21

Compound 20 (7.38×10$^{-4}$ mol) was dissolved in water (10 ml). Compound 14 (8.14×10$^{-4}$ mol) was added, followed by addition of CAN (1.62×10$^{-3}$ mol in 1 ml of water). Sodium hydroxide (15% aq.) was added to obtain a pH of between 7 and 8. After five minutes, the solution turned black. The solution is stirred for 24 hours at room temperature and pH 7-8 (by addition of aliquots of sodium hydroxide). The solution was evaporated to dryness and the residue obtained was then taken up in acetone (20 ml) and evaporated again. A black powder having the characteristics below was thus obtained:

Mass (ESI +): 361

TLC: Ethanol 2: H$_2$O 1: HOAc 1; Rf=0.2 (black)

Absorbance (H$_2$O): λ=465 nm, λ=568 nm.

Examples of Dyeing

| Examples | 1 | 2 | 3 | 4 | 5 |
|---|---|---|---|---|---|
| Compound 6 | $2.5 \times 10^{-4}$ mol | | | | |
| Compound 8 | | $2.5 \times 10^{-4}$ mol | | | |
| Compound 9 | | | $2.5 \times 10^{-4}$ mol | | |
| Compound 11 | | | | $2.5 \times 10^{-4}$ mol | |
| Compound 15 | | | | | $2.5 \times 10^{-4}$ mol |
| Dye support (1) | (*) | (*) | (*) | (*) | (*) |
| Demineralized water qs (g) | 100 | 100 | 100 | 100 | 100 |

(*) Dye support (1) pH 7

| | |
|---|---|
| 96° ethyl alcohol | 20.8 g |
| $C_8$-$C_{10}$ alkyl polyglucoside as an aqueous 60% solution | 12 g |
| Benzyl alcohol | 4.0 g |
| Polyethylene glycol containing 8 ethylene oxide units | 6.0 g |
| $Na_2HPO_4$ | 0.28 g |
| $KH_2PO_4$ | 0.46 g |

A final pH of 7 was obtained.

Each mixture obtained was applied to locks of grey hair containing 90% white hairs. After a leave-in time of 30 minutes, the locks of hair were rinsed, washed with a standard shampoo, rinsed again and then dried.

The following dyeing results were obtained:

| Examples | 1 | 2 | 3 | 4 | 5 |
|---|---|---|---|---|---|
| Shade observed | Strong blue-grey | Strong brown | Strong green-grey | Strong violet-grey | Strong blue-grey |

What is claimed is:

1. A dye composition comprising, in a suitable medium, a compound of formula (I) below:

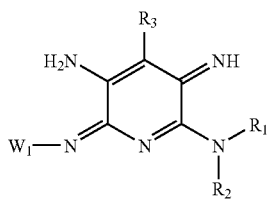

(I)

in which
R$_3$ is chosen from:
a hydrogen atom,
a linear or branched $C_1$-$C_{10}$ hydrocarbon-based chain, which can form at least one 5- to 8-membered carbon-based ring, and which may be saturated or unsaturated, wherein at least carbon atom of the carbon-based chain may be replaced with at least one entity chosen from oxygen, nitrogen and sulfur atoms and $SO_2$ groups, and wherein the carbon atoms may be, independently of each other, substituted with at least one halogen atom; R$_3$ not comprising a peroxide bond or diazo, nitro or nitroso radicals, R$_3$ not being linked to the pyridine ring via an oxygen, nitrogen or sulfur atom;

R$_1$ and R$_2$ are chosen from, independently of each other:
a hydrogen atom,
linear or branched $C_1$-$C_{10}$ hydrocarbon-based chains, which can form at least one 5- to 8-membered carbon-based ring, and which may be saturated or unsaturated, wherein at least one carbon atom of the carbon-based chain may be replaced with at least one entity chosen from oxygen, nitrogen and sulfur atom and $SO_2$ groups, and wherein the carbon atoms may be, independently of each other, substituted with at least one halogen atom; R$_1$ and R$_2$ not comprising a peroxide bond or diazo, nitro or nitroso radicals, and R$_1$ and R$_2$ not being directly linked to the nitrogen atom via an oxygen, sulfur or nitrogen atom
a cationic radical -D-Z in which Z is an onium radical and D is a linear or branched $C_1$-$C_{14}$ hydrocarbon-based chain, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and $SO_2$ groups; the arm D not being linked to the nitrogen atom via a nitrogen, oxygen or sulfur atom;
R$_1$ and R$_2$ form, together with the nitrogen atom to which they are attached, a ring of formula (IV):

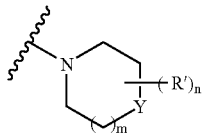

(IV)

in which
R' is chosen from:
a halogen atom;
a $C_1$-$C_4$ alkyl radical optionally substituted with at least one radicals chosen from hydroxyl, carboxyl, $C_1$-$C_4$ alkoxycarbonyl, $(C_1$-$C_4)$alkylamido($(C_1$-$C_4)$alkyl-CONH—), $(C_1$-$C_4)$alkylcarboxamido, $((C_1$-$C_4)$alkylNHCO—), $(C_1$-$C_4)$alkylsulfonyl $((C_1$-$C_4)$alkylSO$_2$—), $C_1$-$C_4$ alkoxy, $(C_1$-$C_4)$ alkylsulfonamido $((C_1$-$C_4)$alkylSO$_2$NH—) and $(C_1$-$C_4)$alkylsulfamoyl $((C_1$-$C_4)$alkylNHSO$_2$—) radicals;
NR'$_3$R'$_4$ with R'$_3$ and R'$_4$, which may be identical or different, being chosen from a hydrogen atom, $C_1$-$C_4$ alkyl radicals optionally substituted with at least one radical chosen from hydroxyl, $C_1$-$C_4$ alkoxy, amino, monoalkylamino, dialkylamino, $(C_1$-$C_4)$alkylCO—, $(C_1$-$C_4)$alkylNHCO— and $(C_1$-$C_4)$alkylSO$_2$ radicals;

a carboxyl radical;

a $C_1$-$C_4$ alkoxycarbonyl radical;

a $(C_1$-$C_4)$alkylamido radical $((C_1$-$C_4)$alkylCONH—);

a $(C_1$-$C_4)$alkylsulfonyl radical (alkylSO$_2$—);

an alkylsulfonamido radical $((C_1$-$C_4)$alkylSO$_2$NH—);

a hydroxyl radical;

a $C_1$-$C_4$ alkoxy radical;

a $C_2$-$C_4$ hydroxyalkoxy radical;

a $(C_1$-$C_4)$alkylcarboxamido radical $((C_1$-$C_4)$alkylN-HCO—);

a $(C_1$-$C_4)$alkylsulfamoyl $((C_1$-$C_4)$alkyl-NH—SO$_2$—);

a $C_1$-$C_4$ thioether radical;

a sulfonic radical (SO$_3$H), which may be in salt form;

a cationic radical -D1-Z in which D1 is a covalent bond or D, n is an integer from 0 to 12, m is an integer from 0 to 2, Y is chosen from a carbon atom, an oxygen atom, a radical NR'$_5$ and a radical NR'$_6$R'$_7$ with R'$_5$ having the same meaning as R'$_3$; R'$_6$ and R'$_7$ have the same meaning as R'$_3$ and are other than a hydrogen atom, with the proviso that when n>1, the radicals R' may be different from each other, W$_1$ is an aromatic heterocyclic radical chosen from the following radicals:

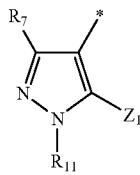

(RI)

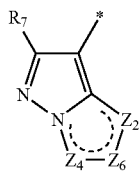

(RII)

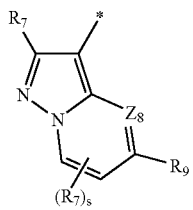

(RIII)

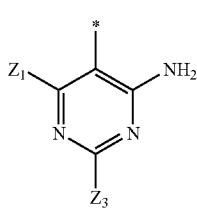

(RIV)

-continued

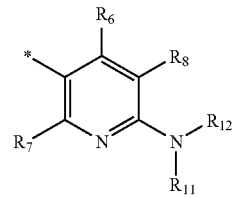

(RV)

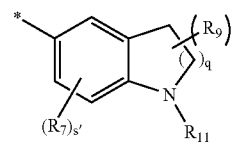

(RVI)

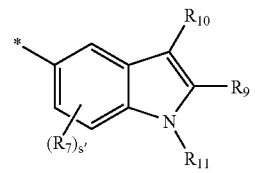

(RVII)

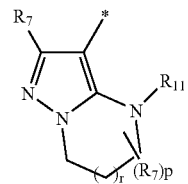

(RVIII)

in which s is 0, 1 or 2, s' is 0, 1, 2 or 3,

Z$_1$ and Z$_3$ are chosen from, independently of each other, a hydroxyl radical and NR$_{11}$R$_{12}$ radicals, Z$_2$, Z$_4$ and Z$_6$ are chosen from, independently of each other, a nitrogen atom, CR$_{12}$ radicals, and NR$_{11}$ radicals, with the proviso that at least one of Z$_2$, Z$_4$ and Z$_6$ is chosen from a radical CR$_{12}$ and that there are not more than three contiguous nitrogen atoms, Z$_8$ is chosen from a nitrogen atom and a radical CR$_{12}$, R$_6$ and R$_8$, independently of each other, have the same meanings as R$_3$, R$_7$, R$_9$, R$_{10}$, R$_{11}$ and R$_{12}$ are chosen from, independently of each other:

a hydrogen atom, linear or branched C$_1$-C$_{10}$ hydrocarbon-based chains, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and SO$_2$ groups, and wherein the carbon atoms may be, independently of each other, substituted with at least one halogen atom; the radicals R$_7$ and R$_9$ to R$_{12}$ not comprising a peroxide bond or diazo or nitroso radicals, and the radicals R$_{11}$ and R$_{12}$ not being directly linked to the nitrogen atom via an oxygen, sulfur or nitrogen atom, with the proviso that the radicals R$_7$ and R$_9$ may be independent of each other, p ranges from 4 to 8, q ranges from 1 to 3, and r ranges from 0 to 2,

* indicates the point of attachment of W$_1$ in formula (I), with the proviso that the compound of formula (I) cannot comprise more than one cationic radical D1-Z.

2. The dye composition according to claim 1, wherein, in compound (I), $R_3$ is chosen from a hydrogen atom and a $C_1$-$C_4$ alkyl radical optionally substituted with at least one radical chosen from hydroxyl, $C_1$-$C_2$ alkoxy, amino and (mono)- or (di)($C_1$-$C_2$)alkylamino radicals.

3. The dye Composition according to claim 1, wherein, in compound (I), $R_3$ is chosen from a hydrogen atom and a methyl, ethyl or 2-hydroxyethyl radical.

4. The dye composition according to claim 1, wherein, in compound (I), $R_1$ and $R_2$ are independently chosen from hydrogen; $C_1$-$C_6$ alkyl radicals optionally substituted with at least one radical chosen from hydroxyl, alkoxy, amino, (mono)-($C_1$-$C_4$)alkylamino, and (di)($C_1$-$C_4$)alkylamino radicals; and a cationic radical -D-Z.

5. The dye composition according to claim 4, wherein, in compound (I), $R_1$ and $R_2$ are independently a radical D-Z with Z chosen from an imidazolium, a tri($C_1$-$C_4$)alkylammonium, a pyridinium and a piperidinium.

6. The dye composition according to claim 1, wherein, in (I), $R_1$ and $R_2$ are independently chosen from hydrogen, methyl, ethyl, hydroxyethyl, propyl, propylimidazolium and propyltrimethylammonium radicals.

7. The dye composition according to claim 1, wherein, in compound (I), $R_1$ and $R_2$ form, with the nitrogen atom to which they are attached, a 5- to 8-membered heterocycle chosen from pyrrolidine, piperidine, homopiperidine, piperazine, homopiperazine and diazepane heterocycles.

8. The dye composition according to claim 7, wherein, in compound (I), $R_1$ and $R_2$ form a heterocycle chosen from pyrrolidine, 3-hydroxypyrrolidine, 3-aminopyrrolidine, 3-N,N-dimethylaminopyrrolidine, 3-acetamidopyrrolidine, 3-(methysulfonylamino)pyrrolidine, proline, 3-hydroxyproline, 3-(N-methylimidazolium)pyrrolidine, 3-(trialkyl($C_1$-$C_4$)ammonium)pyrrolidine, piperidine, hydroxypiperidine, homopiperidine, diazepane, N-methylhomopiperazine and N-β-hydroxyethylhomopiperazine, and the addition salts thereof.

9. The dye composition according to claim 8, wherein, in compound (I), $R_1$ and $R_2$ form, with the nitrogen atom to which they are attached, an optionally substituted pyrrolidine ring.

10. The dye composition according to claim 1, wherein, in the compound of formula (I), the cationic radical -D-Z corresponds to formula (V) below:

(V)

in which
D is as defined in claim 1,
$R_{17}$, $R_{18}$ and $R_{19}$, independently of each other, are chosen from $C_1$-$C_{15}$ alkyl radicals; $C_1$-$C_6$ monohydroxyalkyl radicals; $C_2$-$C_6$ polyhydroxyalkyl radicals; ($C_1$-$C_6$)alkoxy($C_1$-$C_6$)alkyl radicals; aryl radicals; benzyl radicals; $C_1$-$C_6$ amidoalkyl radicals; tri($C_1$-$C_6$)alkylsilane($C_1$-$C_6$)alkyl radicals; $C_1$-$C_6$ aminoalkyl radicals; $C_1$-$C_6$ aminoalkyl radicals in which the amine is mono- or disubstituted with at least one radical chosen from $C_1$-$C_4$ alkyl, ($C_1$-$C_6$)alkylcarbonyl, acylamino and ($C_1$-$C_6$)alkylsulfonyl radicals;
$R_{17}$, $R_{18}$ and $R_{19}$ together, in pairs, may form, with the quaternized nitrogen atom to which they are attached, a 5-, 6- or 7-membered carbon-based saturated ring which may contain at least one hetero atom, wherein the cationic ring may be substituted with at least one entity chosen from halogen atoms, hydroxyl radicals, $C_1$-$C_6$ alkyl radicals, $C_1$-$C_6$ monohydroxyalkyl radicals, $C_2$-$C_6$ polyhydroxyalkyl radicals, $C_1$-$C_6$ alkoxy radicals, tri($C_1$-$C_6$)alkylsilane($C_1$-$C_6$)alkyl radicals, amido radicals, carboxyl radicals, $C_1$-$C_6$ alkylcarbonyl radicals, thio radicals, $C_1$-$C_6$ thioalkyl radicals, ($C_1$-$C_6$) alkylthio radicals, amino radicals, and amino radicals mono- or disubstituted with at least one radical chosen from ($C_1$-$C_6$)alkyl, ($C_1$-$C_6$)alkylcarbonyl, acylamino and ($C_1$-$C_6$)alkylsulfonyl radicals;
one from among $R_{17}$, $R_{18}$ and $R_{19}$ may be linked to one of the carbon or nitrogen atoms of the arm D to form a 5- to 7-membered ring, and
$X^-$ is a counterion.

11. The dye composition according to claim 10, in which $R_{17}$, $R_{18}$ and $R_{19}$, independently of each other, are chosen from $C_1$-$C_6$ alkyl radicals, $C_1$-$C_4$ monohydroxyalkyl radicals, $C_2$-$C_4$ polyhydroxyalkyl radicals, ($C_2$-$C_6$)alkoxy($C_1$-$C_4$)alkyl radicals, $C_2$-$C_6$ amidoalkyl radicals and tri($C_1$-$C_6$)alkylsilane($C_1$-$C_6$)alkyl radicals.

12. The dye composition according to claim 10, in which $R_{17}$ and $R_{18}$ together form a ring chosen from pyrrolidinium, piperidinium, homopiperidinium, piperazinium, homopiperazinium and morpholinium rings, and $R_{19}$ is chosen from a $C_1$-$C_6$ alkyl radical; a $C_1$-$C_6$ monohydroxyalkyl radical; a $C_2$-$C_6$ polyhydroxyalkyl radical; a $C_2$-$C_6$ aminoalkyl radical; an aminoalkyl radical mono- or disubstituted with at least one radical chosen from ($C_1$-$C_6$)alkyl radicals and ($C_1$-$C_6$)alkylcarbonyl radicals; a $C_2$-$C_6$ carbamylalkyl radical; a tri($C_1$-$C_6$)alkylsilane($C_1$-$C_6$)alkyl radical; a ($C_1$-$C_6$) alkylcarboxy($C_1$-$C_6$)alkyl radical; a ($C_1$-$C_6$)alkylcarbonyl ($C_2$-$C_6$)alkyl radical; and an N—($C_1$-$C_6$)alkylcarbamyl($C_2$-$C_6$)alkyl radical.

13. The dye composition according to claim 10, in which $R_{17}$, $R_{18}$ and $R_{19}$ are alkyl radicals.

14. The dye composition according to claim 10, in which D is a $C_1$-$C_6$ alkylene chain that may be substituted.

15. The dye composition according to claim 1, in which the cationic radical -D-Z corresponds to formula (VI)

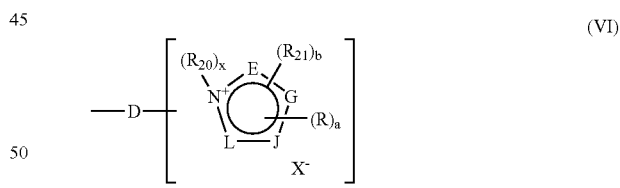

(VI)

in which
D is as defined in claim 1,
the ring members E, G, J and L, which may be identical or different, are chosen from carbon, oxygen, sulfur and nitrogen atoms to form a ring chosen from pyrazolium, imidazolium, triazolium, oxazolium, isoxazolium, thiazolium and isothiazolium rings,
a is an integer ranging from 1 to 3;
b is 0 or 1;
R, which may be identical or different, is chosen from a hydrogen atom, a halogen atom, a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, an amido radical, a carboxyl radical, a $C_1$-$C_6$ alkylcarbonyl radical, a $C_1$-$C_6$ thioalkyl radical, a ($C_1$-$C_6$)alkylthio radical, an amino radical disubstituted with at least one radical chosen from ($C_1$-$C_6$)alkyl, ($C_1$-$C_6$)alkylcarbonyl and ($C_1$-$C_6$)alkylsulfonyl radicals, a benzyl radical, a phenyl radical optionally substituted with at least one radical chosen from methyl, hydroxyl, amino and methoxy radicals; with the proviso that the radicals R are borne by a carbon atom, $R_{21}$ is chosen from a $C_1$-$C_6$ alkyl radical, a $C_1$-$C_6$ monohydroxyalkyl radical, a $C_2$-$C_6$ polyhydroxyalkyl radical, a tri($C_1$-$C_6$)alkylsilane($C_1$-$C_6$)alkyl radical, a ($C_1$-$C_6$)alkoxy($C_1$-$C_6$)alkyl radical, a $C_2$-$C_6$ carbamylalkyl radical, a ($C_1$-$C_6$)alkylcarboxy($C_1$-$C_6$)alkyl radical or a benzyl radical; with the proviso that the radical $R_{21}$ is borne by a nitrogen atom, $R_{20}$ is chosen from a $C_1$-$C_6$ alkyl radical; a $C_1$-$C_6$ monohydroxyalkyl radical; a $C_2$-$C_6$ polyhydroxyalkyl radical; a ($C_1$-$C_6$)aminoalkyl radical; a benzyl radical; a ($C_1$-$C_6$)aminoalkyl radical in which the amine is mono- or disubstituted with at least one radical chosen from ($C_1$-$C_6$)alkyl, ($C_1$-$C_6$)alkylcarbonyl, acylamino and ($C_1$-$C_6$)alkylsulfonyl radicals; a carboxy($C_1$-$C_6$)alkyl radical; a carbamyl($C_1$-$C_6$)alkyl radical; a ($C_2$-$C_6$)trifluoroalkyl radical; a tri($C_1$-$C_6$)alkylsilane($C_1$-$C_6$)alkyl radical; a sulfonamido($C_2$-$C_6$)alkyl radical; a ($C_1$-$C_6$)alkylcarboxy($C_1$-$C_6$)alkyl radical; a ($C_1$-$C_6$)alkylsulfinyl($C_2$-$C_6$)alkyl radical; a ($C_1$-$C_6$)alkylsulfonyl($C_2$-$C_6$)alkyl radical; a ($C_1$-$C_6$)alkylcarbonyl($C_2$-$C_6$)alkyl radical; an N—($C_1$-$C_6$)alkylcarbamyl($C_2$-$C_6$)alkyl radical; and an N—($C_1$-$C_6$)alkylsulfonamido($C_2$-$C_6$)alkyl radical;

x is equal to 0 or 1,
when x=0, the linker arm D is attached to the ammonium atom,
when x=1, the linker arm D is attached to one of the ring members E, G, J or L,
$X^-$ is a counterion.

16. The dye composition according to claim 15, in which the ring members E, G, J and L form a ring chosen from imidazolium, pyrazolium, oxazolium, thiazolium and triazolium rings.

17. The dye composition according to claim 15, wherein, in formula (VI), x is equal to 0 and D is a $C_1$-$C_4$ hydrocarbon-based chain that may be substituted.

18. The dye composition according to claim 1, in which the cationic radical -D-Z corresponds to formula (VII)

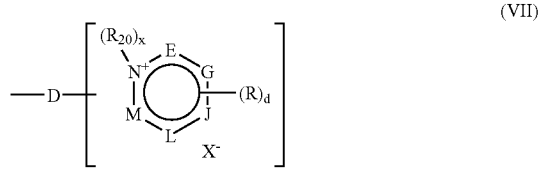

(VII)

in which
D is as defined in claim 1,
R and $R_{20}$ are as defined in claim 17,
the ring members E, G, J, L and M, which may be identical or different, are chosen from carbon and nitrogen atoms and form a ring chosen from pyridinium, pyrimidinium, pyrazinium and pyridazinium rings,
d is an integer ranging from 1 to 5,
x is equal to 0 or 1,
when x=0, the linker arm D is attached to the ammonium atom,
when x=1, the linker arm D is attached to one of the ring members E, G, J, L or M,
$X^-$ is a counterion.

19. The dye composition according to claim 18, in which, in formula (VII), the ring members E, G, J, L and M form, with the quaternized nitrogen of the ring, a ring chosen from pyridinium, pyrimidinium, pyrazinium and pyridazinium rings.

20. The dye composition according to claim 18, in which, in formula (VII), x is equal to 0 and R is chosen from a hydrogen atom, a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, a $C_1$-$C_6$ alkylcarbonyl radical, an amino radical disubstituted with at least one radical chosen from ($C_1$-$C_6$)alkyl, ($C_1$-$C_6$)alkylcarbonyl and ($C_1$-$C_6$)alkylsulfonyl radicals; with the proviso that the radicals R are borne by a carbon atom.

21. The dye composition according to claim 18, in which, in formula (VII), x is equal to 1, $R_{20}$ is chosen from a $C_1$-$C_6$ alkyl radical; a $C_1$-$C_6$ monohydroxyalkyl radical; a $C_2$-$C_6$ polyhydroxyalkyl radical; a $C_2$-$C_6$ aminoalkyl radical, a $C_2$-$C_6$ aminoalkyl radical in which the amine is mono- or disubstituted with at least one radical chosen from ($C_1$-$C_6$) alkyl, ($C_1$-$C_6$)alkylcarbonyl, acylamino and ($C_1$-$C_6$)alkylsulfonyl radicals; a $C_1$-$C_6$ carbamylalkyl radical; a ($C_1$-$C_6$) alkylcarbonyl($C_1$-$C_6$)alkyl radical; an N—($C_1$-$C_6$) alkylcarbamyl($C_1$-$C_6$)alkyl radical; R is chosen from a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, a $C_1$-$C_6$ alkylcarbonyl radical, an amino radical disubstituted with at least one radical chosen from ($C_1$-$C_6$)alkyl, ($C_1$-$C_6$) alkylcarbonyl and($C_1$-$C_6$)alkylsulfonyl radicals.

22. The dye composition according to claim 20, in which, in formula (VII), $R_{20}$ is a $C_1$-$C_4$ alkyl radical that may be substituted with a hydroxyl or methoxy radical, and R is chosen from hydrogen radical and a $C_1$-$C_4$ alkyl radical that may be optionally substituted with a hydroxyl or methoxy radical.

23. The dye composition according to claim 21, in which, in formula (VII), $R_{20}$ is a $C_1$-$C_4$ alkyl radical that may be substituted with a hydroxyl or methoxy radical, and R is chosen from a hydrogen and a $C_1$-$C_4$ alkyl radical that may be optionally substituted with a hydroxyl or methoxy radical.

24. The dye composition according to claim 1, in which $W_1$ is chosen from 5-aminopyrazole, 5-hydroxypyrazole, pyrazolo[1,5-a]pyridine, pyrazolo[1,5-a]pyrimidine, triaminopyrimidine and 2,3-diamino-6-alkoxypyridine radicals.

25. The dye composition according to claim 24, in which $W_1$ is chosen from 5-aminopyrazole and 5-hydroxypyrazole radicals.

26. The dye composition according to claim 25, in which $W_1$ is chosen from 5-aminopyrazole and 5-hydroxypyrazole radicals with $R_7$ and $R_{11}$ chosen independently from a hydrogen atom; a linear or branched $C_1$-$C_4$ hydrocarbon-based chain that can form at least one 5- or 6-membered carbon-based ring and that may be saturated or unsaturated, wherein the carbon atoms may be, independently of each other, substituted with at least one entity chosen from halogen atoms, hydroxyl radicals, and amino radicals; a $C_1$-$C_2$ alkoxy radical; an amino radical; and a (di)($C_1$-$C_4$) alkylamino radical.

27. The dye composition according to claim 24, in which $W_1$ is

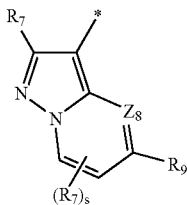

(RIII)

$Z_8$ is chosen from a nitrogen atom and a radical $CR_{12}$.
$R_7$, $R_9$, and $R_{12}$ are chosen from, independently of each other:
a hydrogen atom,
linear or branched $C_1$-$C_{10}$ hydrocarbon-based chains, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and $SO_2$ groups, and wherein the carbon atoms may be, independently of each other, substituted with at least one halogen atom; with the proviso that $R_7$, $R_9$, and $R_{12}$ do not comprise not comprising a peroxide bond or diazo or nitroso radicals, and $R_{12}$ is not directly linked to the nitrogen atom via an oxygen, sulfur or nitrogen atom.

28. The dye composition according to claim 27, in which, in $W_1$, $Z_8$ represents $CR_{12}$, and $R_7$, $R_9$ and $R_{12}$, which may be identical or different, are chosen from:
a hydrogen atom,
amino radicals,
linear or branched $C_1$-$C_8$ hydrocarbon-based chains, which may form at least one 5- to 8-membered carbon-based ring, and which may be saturated or unsaturated, wherein at least one carbon atom of the carbon-based chain may be replaced with at least one entity chosen from oxygen, nitrogen and sulfur atoms and $SO_2$ groups, and wherein the carbon atoms may be, independently of each other, substituted with at least one halogen atom; the radicals not comprising a peroxide bond or diazo or nitroso radicals, and not being linked directly to the nitrogen atom via an oxygen, sulfur or nitrogen atom.

29. The dye composition according to claim 28, in which the radicals $R_7$, $R_9$ and $R_{12}$ are chosen from a hydrogen atom; linear or branched $C_1$-$C_4$ hydrocarbon-based chains that may be saturated or unsaturated, the carbon atoms of which may be, independently of each other, substituted with at least one entity chosen from halogen atoms and hydroxyl and amino radicals; $C_1$-$C_2$ alkoxy radicals; amino radicals; and optionally substituted (di)($C_1$-$C_4$)alkylamino radicals.

30. The dye composition according to claim 27, in which, in $W_1$, $Z_8$ is N and $R_7$ and $R_9$ are chosen independently from a hydrogen atom; linear or branched $C_1$-$C_6$ alkyl radicals; $C_1$-$C_6$ monohydroxyalkyl radicals; $C_2$-$C_6$ polyhydroxyalkyl radicals; $C_1$-$C_6$ aminoalkyl radicals, $C_1$-$C_6$ aminoalkyl radicals in which the amine is mono- or disubstituted with at least one radical chosen from ($C_1$-$C_6$)alkyl and ($C_1$-$C_6$) alkylcarbonyl radicals; hydroxyl radicals; amino radicals, wherein the amino may be substituted with at least one linear or branched $C_1$-$C_{10}$ alkyl radical, which can form at least one 5- to 6-membered carbon-based ring, and which may be saturated or unsaturated, the carbon atoms of which may be, independently of each other, substituted with at least one entity chosen from halogen atoms, hydroxyl radicals, and amino radicals; and $C_1$-$C_2$ alkoxy radicals.

31. The dye composition according to claim 27, in which $R_7$, $R_9$ and $R_{12}$ are chosen from hydrogen, $C_1$-$C_4$ alkyl radicals, amino radicals, $C_1$-$C_4$ monoalkylamino radicals; $C_1$-$C_4$ dialkylamino radicals, $C_1$-$C_4$ hydroxyalkyl radicals; and $C_1$-$C_4$ alkoxy radicals.

32. The dye composition according to claim 1, in which the compound of formula (I) is a cationic compound substituted with a cationic radical D-Z.

33. The dye composition according to claim 1, in which at least one of the radicals $R_1$ and $R_2$ is a cationic radical -D-Z.

34. The dye composition according to claim 1, in which $R_1$ and $R_2$ form the ring of formula (IV) in which R' is a cationic radical D1-Z.

35. The dye composition according to claim 34, in which R' is chosen from an imidazolium and a trialkylammonium.

36. The dye composition according to claim 1, in which Y is $N'R'_6R'_7$, and $R'_6$ and $R'_7$ are independently chosen from $C_1$-$C_4$ alkyl radicals.

37. The dye composition according to claim 1, in which the compound of formula (I) is chosen from:

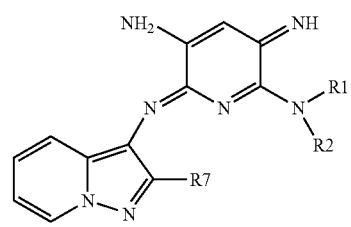

Ia

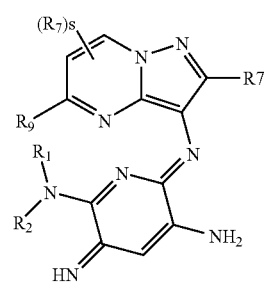

Ib

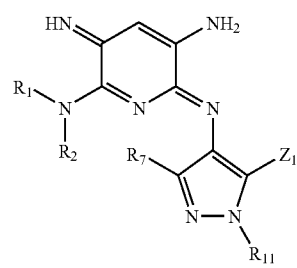

Ic

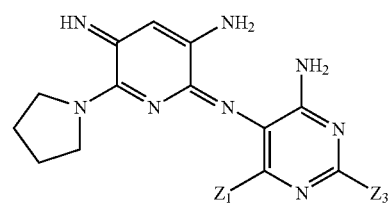

Id in which $R_1$, $R_2$, $R_6$, $R_7$, $R_8$, $R_9$, $R_{11}$, $Z_1$, $Z_2$ and $Z_3$ are as defined as in claim 1.

38. The dye composition according to claim 1, in which the compound of formula (I) is chosen from
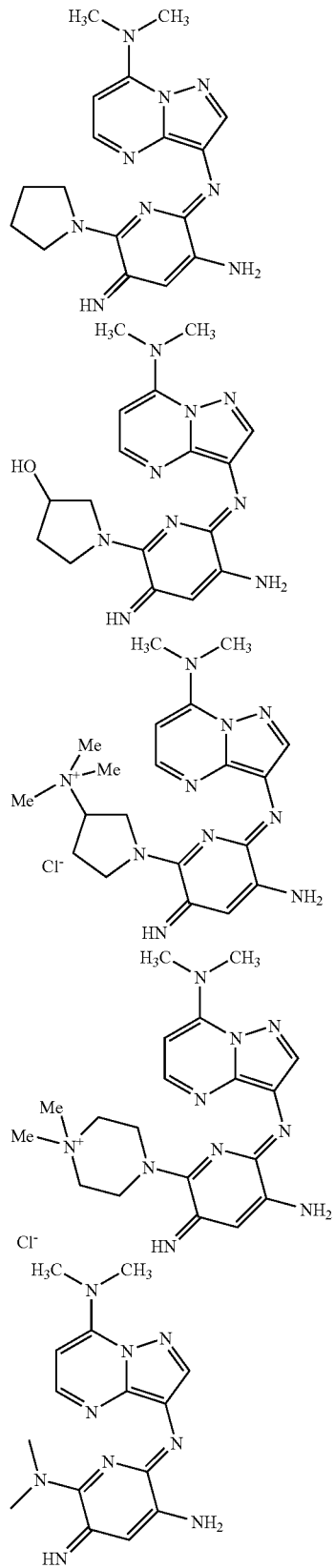
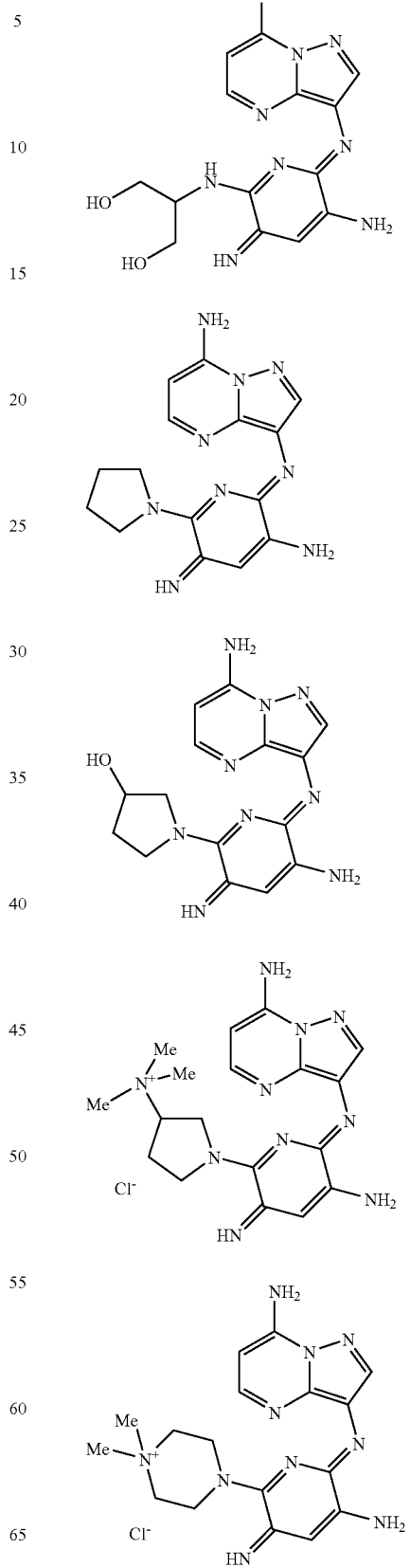

-continued
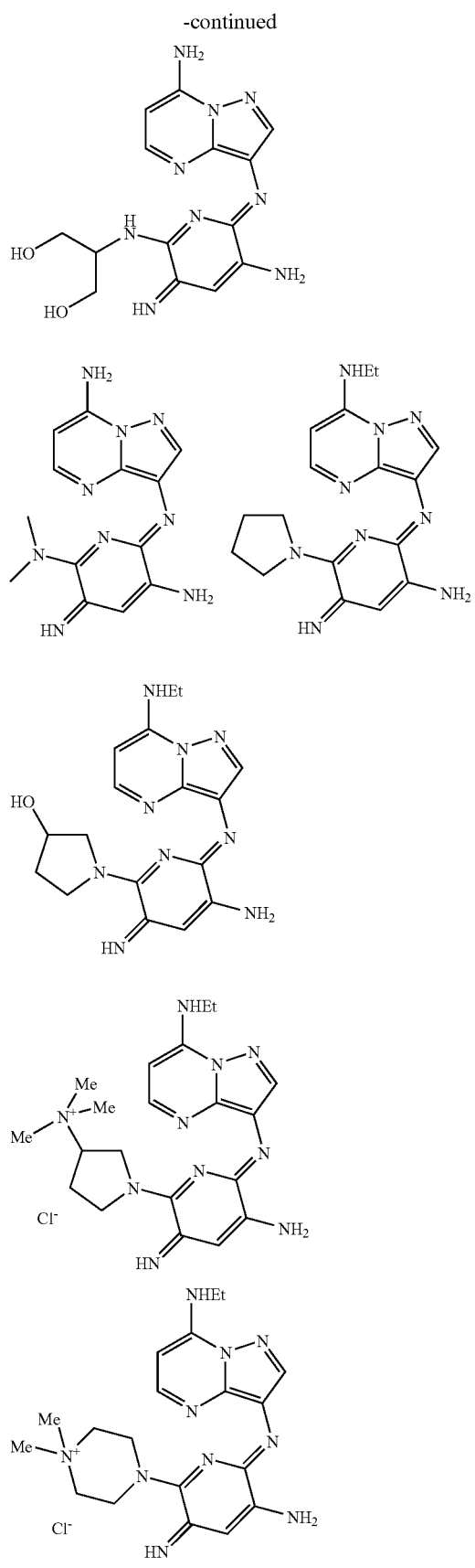
-continued
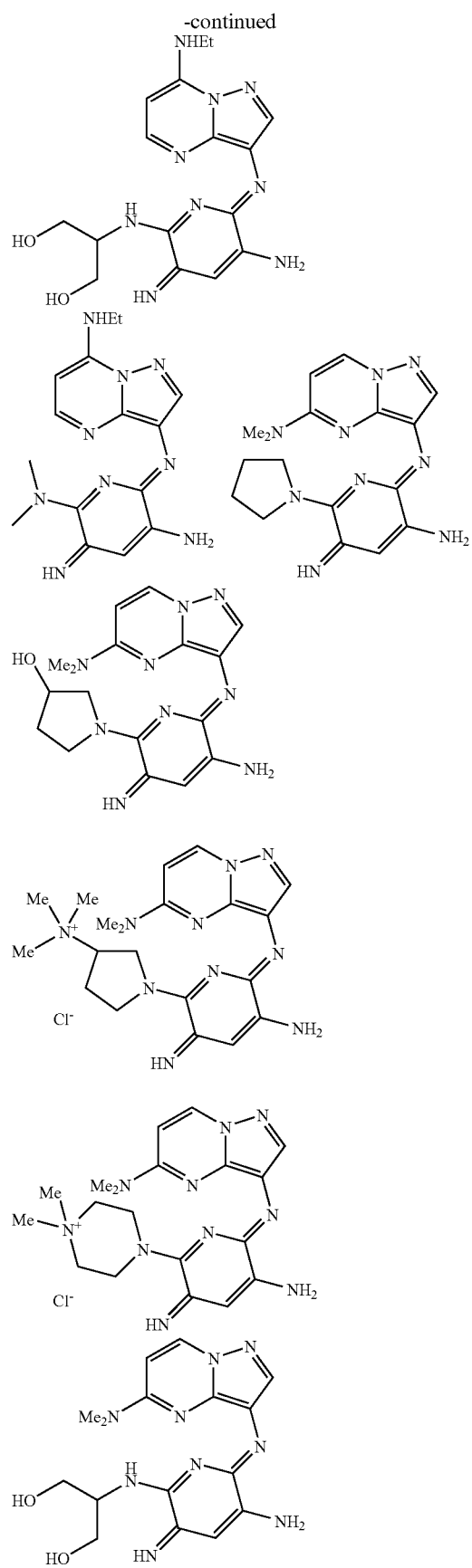

-continued
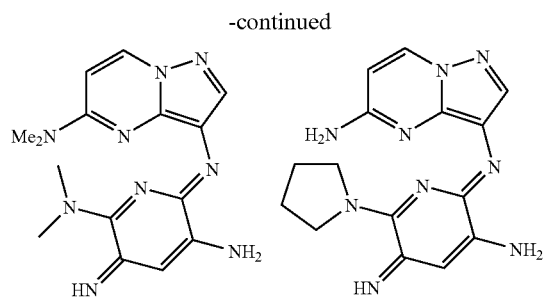
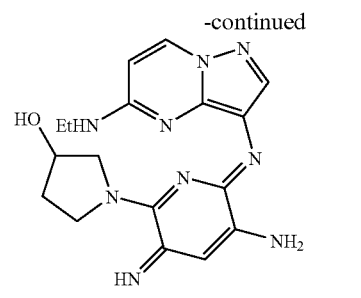
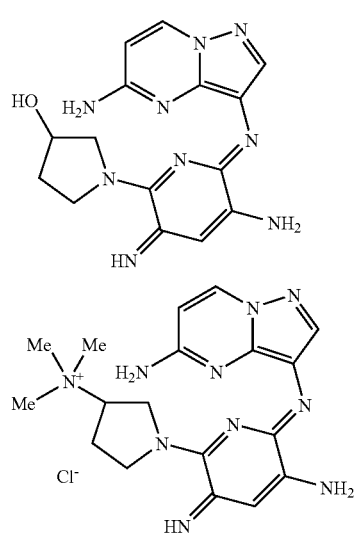
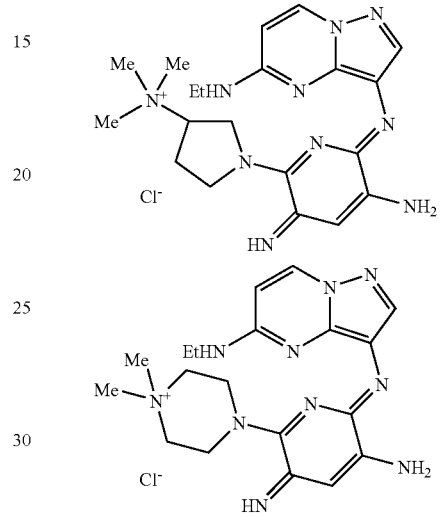
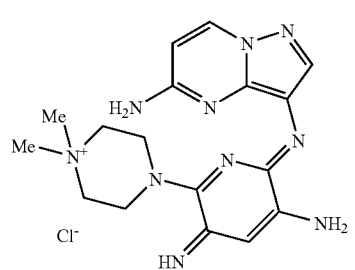
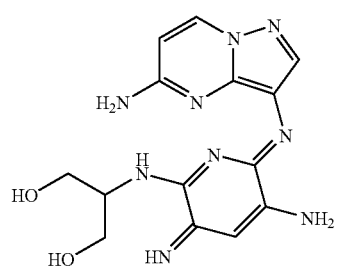
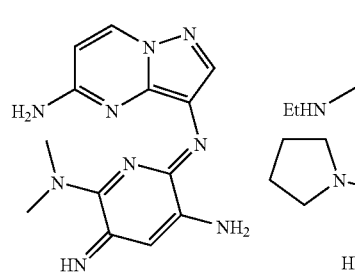
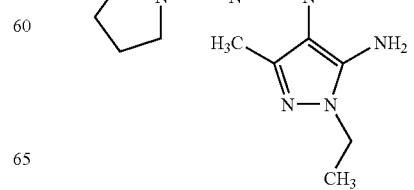

-continued
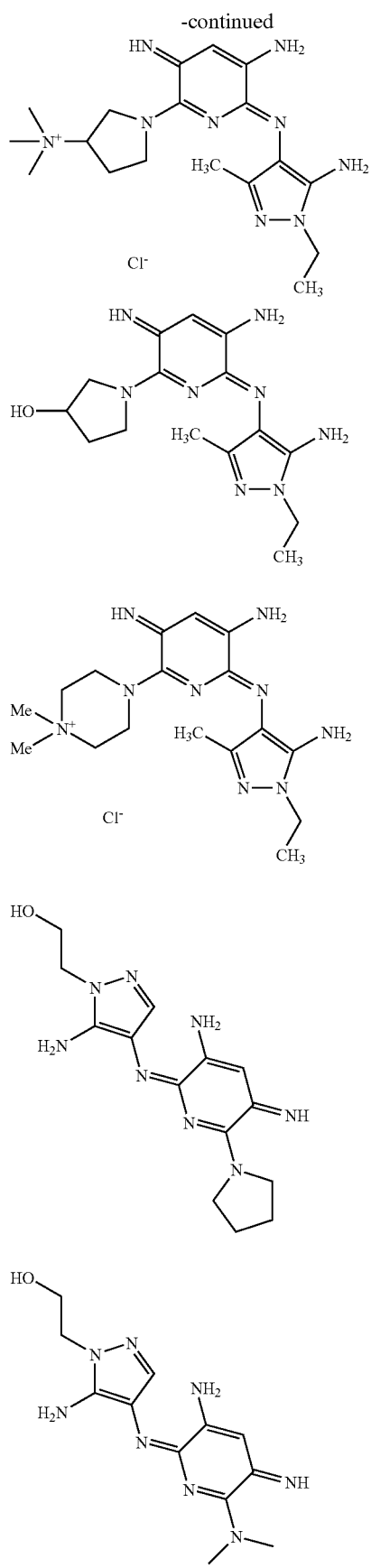
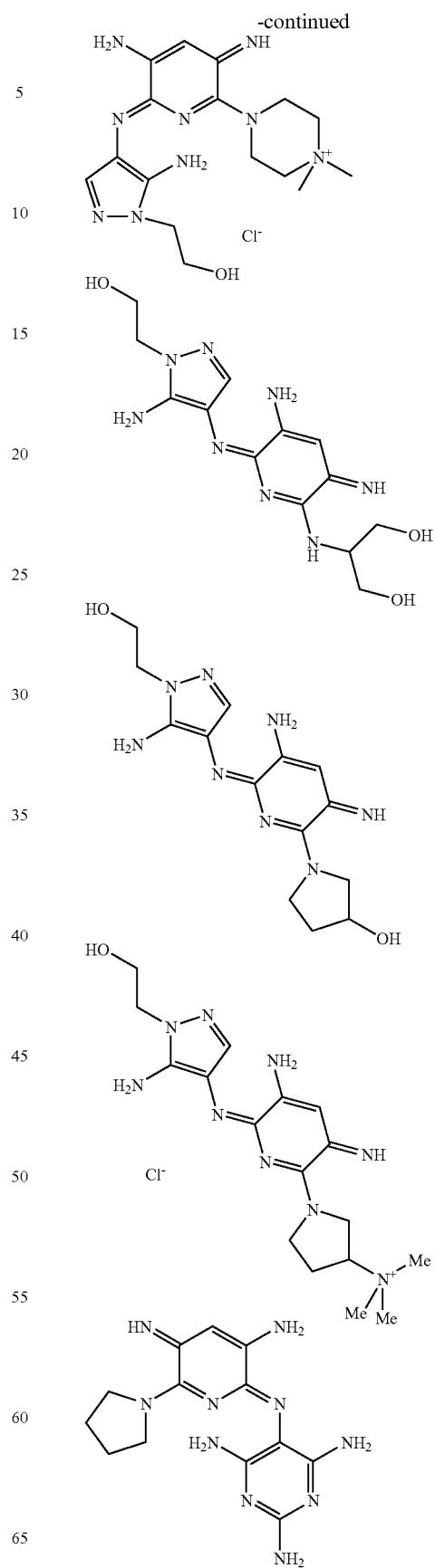

-continued

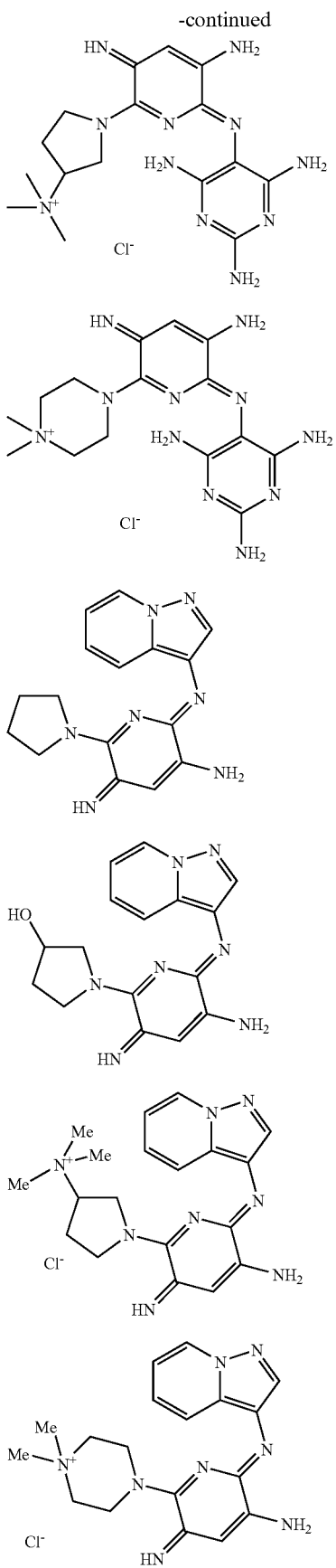

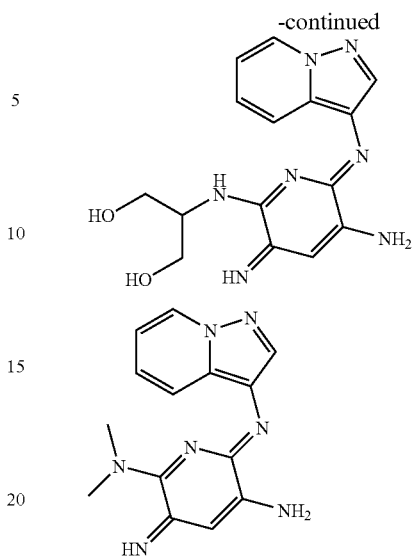

39. The dye composition according claim 1, in which the dye of formula (I) is present in an amount ranging from 0.01% to 10% by weight, relative to the total weight of the composition.

40. The dye composition according to claim 1, further comprising at least one oxidation base chosen from para-phenylenediamines, bis(phenyl)alkylenediamines, para-aminophenols, ortho-aminophenols and heterocyclic bases, and the acid-addition salts thereof.

41. The dye composition according to claim 40, in which the at least one oxidation base is present in an amount ranging from 0.001% to 10% by weight, relative to the total weight of the composition.

42. The dye composition according to claim 1, comprising at least one coupler chosen from meta-phenylenediamines, meta-aminophenols, meta-diphenols, naphthalene-based couplers and heterocyclic couplers, and the acid-addition salts thereof.

43. The dye composition according to claim 1, further comprising at least one oxidizing agent.

44. A direct dye compound of formula (I):

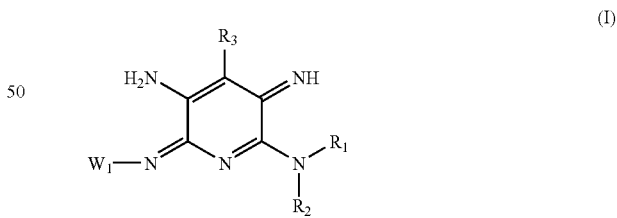

in which
R$_3$ is chosen from:
a hydrogen atom,
a linear or branched C$_1$-C$_{10}$ hydrocarbon-based chain, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and SO$_2$ groups, and wherein the carbon atoms may be, independently of each other, substituted with at least one halogen atom; $R_3$ not comprising a peroxide bond or diazo, nitro or nitroso radicals, $R_3$ not being linked to the pyridine ring via an oxygen, nitrogen or sulfur atom;

$R_1$ and $R_2$ are chosen from, independently of each other:
- a hydrogen atom,
- linear or branched $C_1$-$C_{10}$ hydrocarbon-based chains, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and $SO_2$ groups, and wherein the carbon atoms may be, independently of each other, substituted with at least one halogen atom; $R_1$ and $R_2$ not comprising a peroxide bond or diazo, nitro or nitroso radicals, and $R_1$ and $R_2$ not being directly linked to the nitrogen atom via an oxygen, sulfur or nitrogen atom
- a cationic radical -D-Z in which Z is an onium radical and D is a linear or branched $C_1$-$C_{14}$ hydrocarbon-based chain, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and $SO_2$ groups; the arm D not being linked to the nitrogen atom via a nitrogen, oxygen or sulfur atom;

$R_1$ and $R_2$ form, together with the nitrogen atom to which they are attached, a ring of formula (IV):

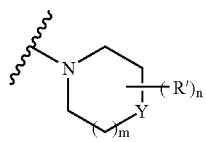

(IV)

in which
R' is chosen from:
- a halogen atom;
- a $C_1$-$C_4$ alkyl radical optionally substituted with at least one radicals chosen from hydroxyl, carboxyl, $C_1$-$C_4$ alkoxycarbonyl, ($C_1$-$C_4$)alkylamido(($C_1$-$C_4$)alkylCONH—), ($C_1$-$C_4$)alkylcarboxamido, (($C_1$-$C_4$)alkylNHCO—), ($C_1$-$C_4$)alkylsulfonyl (($C_1$-$C_4$)alkylSO$_2$—), $C_1$-$C_4$ alkoxy, ($C_1$-$C_4$)alkylsulfonamido (($C_1$-$C_4$)alkylSO$_2$NH—) and ($C_1$-$C_4$)alkylsulfamoyl (($C_1$-$C_4$)alkylNHSO$_2$—) radicals;
- NR'$_3$R'$_4$ with R'$_3$ and R'$_4$, which may be identical or different, being chosen from a hydrogen atom, $C_1$-$C_4$ alkyl radicals optionally substituted with at least one radical chosen from hydroxyl, $C_1$-$C_4$ alkoxy, amino, monoalkylamino, dialkylamino, ($C_1$-$C_4$)alkylCO—, ($C_1$-$C_4$)alkylNHCO— and ($C_1$-$C_4$)alkylSO$_2$ radicals;
- a carboxyl radical;
- a $C_1$-$C_4$ alkoxycarbonyl radical;
- a ($C_1$-$C_4$)alkylamido radical (($C_1$-$C_4$)alkylCONH—);
- a ($C_1$-$C_4$)alkylsulfonyl radical (alkylSO$_2$—);
- an alkylsulfonamido radical (($C_1$-$C_4$)alkylSO$_2$NH—);
- a hydroxyl radical;
- a $C_1$-$C_4$ alkoxy radical;
- a $C_2$-$C_4$ hydroxyalkoxy radical;
- a ($C_1$-$C_4$)alkylcarboxamido radical (($C_1$-$C_4$)alkylNHCO—);
- a ($C_1$-$C_4$)alkylsulfamoyl (($C_1$-$C_4$)alkyl-NH—SO$_2$—);
- a $C_1$-$C_4$ thioether radical;
- a sulfonic radical (SO$_3$H), which may be in salt form;
- a cationic radical -D1-Z in which D1 is a covalent bond or D, n is an integer from 0 to 12,
m is an integer from 0 to 2,
Y is chosen from a carbon atom, an oxygen atom, a radical NR'$_5$ and a radical NR'$_6$R'$_7$ with R'$_5$ having the same meaning as R'$_3$; R'$_6$ and R'$_7$ have the same meaning as R'$_3$ and are other than a hydrogen atom,
with the proviso that when n>1, the radicals R' may be different from each other, $W_1$ is an aromatic heterocyclic radical chosen from the following radicals:

(RI)

(RII)

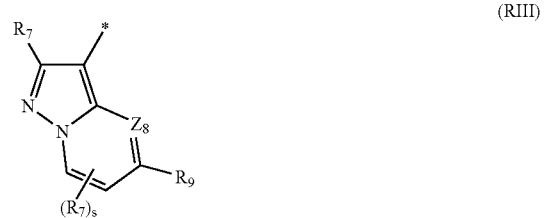

(RIII)

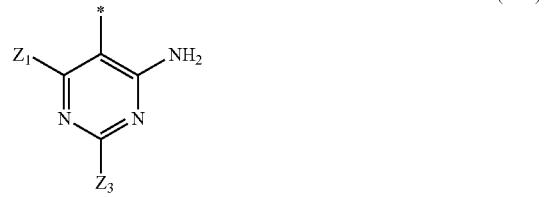

(RIV)

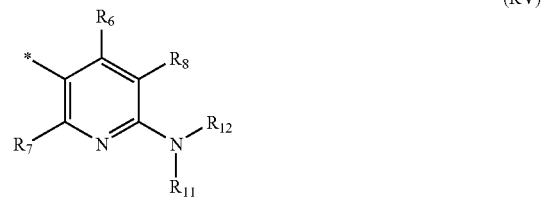

(RV)

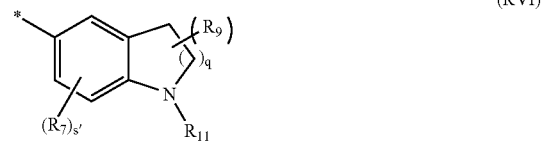

(RVI)

-continued (RVII)

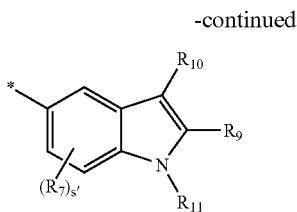

(RVIII)

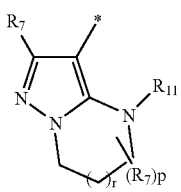

in which
s is 0, 1 or 2,
s' is 0, 1, 2 or 3,
$Z_1$ and $Z_3$ are chosen from, independently of each other, a hydroxyl radical and $NR_{11}R_{12}$ radicals,
$Z_2$, $Z_4$ and $Z_6$ are chosen from, independently of each other, a nitrogen atom, $CR_{12}$ radicals, and $NR_{11}$ radicals, with the proviso that at least one of $Z_2$, $Z_4$ and $Z_6$ is chosen from a radical $CR_{12}$ and that there are not more than three contiguous nitrogen atoms,
$Z_8$ is chosen from a nitrogen atom and a radical $CR_{12}$,
$R_6$ and $R_8$, independently of each other, have the same meanings as $R_3$, $R_7$, $R_9$, $R_{10}$, $R_{11}$ and $R_{12}$ are chosen from, independently of each other:
a hydrogen atom,
linear or branched $C_1$-$C_{10}$ hydrocarbon-based chains, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and $SO_2$ groups, and wherein the carbon atoms may be, independently of each other, substituted with at least one halogen atom; the radicals $R_7$ and $R_9$ to $R_{12}$ not comprising a peroxide bond or diazo or nitroso radicals, and the radicals $R_{11}$ and $R_{12}$ not being directly linked to the nitrogen atom via an oxygen, sulfur or nitrogen atom,
with the proviso that the radicals $R_7$ and $R_9$ may be independent of each other,
p ranges from 4 to 8,
q ranges from 1 to 3, and
r ranges from 0 to 2,
* indicates the point of attachment of $W_1$ in formula (I), with the proviso that the compound of formula (I) cannot comprise more than one cationic radical D1-Z.

45. A process for dyeing keratin fibers, which comprises applying to keratin fibers, for a time sufficient to obtain a desired coloration,
a dye composition comprising a compound of formula (I) below:

(I)

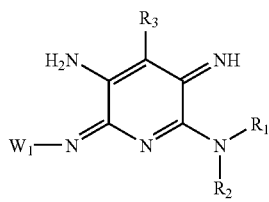

in which
$R_3$ is chosen from:
a hydrogen atom,
a linear or branched $C_1$-$C_{10}$ hydrocarbon-based chain, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and $SO_2$ groups, and wherein the carbon atoms may be, independently of each other, substituted with at least one halogen atom; $R_3$ not comprising a peroxide bond or diazo, nitro or nitroso radicals, $R_3$ not being linked to the pyridine ring via an oxygen, nitrogen or sulfur atom;
$R_1$ and $R_2$ are chosen from, independently of each other:
a hydrogen atom,
linear or branched $C_1$-$C_{10}$ hydrocarbon-based chains, which can form at least one 5- to 8-membered carbon-based ring, and which may be saturated or unsaturated, wherein at least one carbon atom of the carbon-based chain may be replaced with at least one entity chosen from oxygen, nitrogen and sulfur atom and $SO_2$ groups, and wherein the carbon atoms may be, independently of each other, substituted with at least one halogen atom; $R_1$ and $R_2$ not comprising a peroxide bond or diazo, nitro or nitroso radicals, and $R_1$ and $R_2$ not being directly linked to the nitrogen atom via an oxygen, sulfur or nitrogen atom
a cationic radical -D-Z in which Z is an onium radical and D is a linear or branched $C_1$-$C_{14}$ hydrocarbon-based chain, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and $SO_2$ groups; the arm D not being linked to the nitrogen atom via a nitrogen, oxygen or sulfur atom;
$R_1$ and $R_2$ form, together with the nitrogen atom to which they are attached, a ring of formula (IV):

(IV)

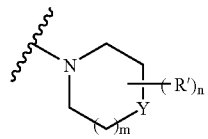

in which
R' is chosen from:
a halogen atom;
a $C_1$-$C_4$ alkyl radical optionally substituted with at least one radicals chosen from hydroxyl, carboxyl, $C_1$-$C_4$ alkoxycarbonyl, $(C_1$-$C_4)$alkylamido$((C_1$-$C_4)$alkyl-CONH—), $(C_1$-$C_4)$alkylcarboxamido, $((C_1$-$C_4)$alkylNHCO—), $(C_1$-$C_4)$alkylsulfonyl $((C_1$-$C_4)$alkylSO$_2$—), $C_1$-$C_4$ alkoxy, $(C_1$-$C_4)$alkylsulfonamido $((C_1$-$C_4)$alkylSO$_2$NH—) and $(C_1$-$C_4)$alkylsulfamoyl $((C_1$-$C_4)$alkylNHSO$_2$—) radicals;

NR'$_3$R'$_4$ with R'$_3$ and R'$_4$, which may be identical or different, being chosen from a hydrogen atom, C$_1$-C$_4$ alkyl radicals optionally substituted with at least one radical chosen from hydroxyl, C$_1$-C$_4$ alkoxy, amino, monoalkylamino, dialkylamino, (C$_1$-C$_4$)alkylCO—, (C$_1$-C$_4$)alkylNHCO— and (C$_1$-C$_4$)alkylSO$_2$ radicals;

a carboxyl radical;

a C$_1$-C$_4$ alkoxycarbonyl radical;

a (C$_1$-C$_4$)alkylamido radical ((C$_1$-C$_4$)alkylCONH—);

a (C$_1$-C$_4$)alkylsulfonyl radical (alkylSO$_2$—);

an alkylsulfonamido radical ((C$_1$-C$_4$)alkylSO$_2$NH—);

a hydroxyl radical;

a C$_1$-C$_4$ alkoxy radical;

a C$_2$-C$_4$ hydroxyalkoxy radical;

a (C$_1$-C$_4$)alkylcarboxamido radical ((C$_1$-C$_4$)alkylNHCO—);

a (C$_1$-C$_4$)alkylsulfamoyl ((C$_1$-C$_4$)alkyl-NH—SO$_2$—);

a C$_1$-C$_4$ thioether radical;

a sulfonic radical (SO$_3$H), which may be in salt form;

a cationic radical -D1-Z in which D1 is a covalent bond or D, n is an integer from 0 to 12, m is an integer from 0 to 2, Y is chosen from a carbon atom, an oxygen atom, a radical NR'$_5$ and a radical NR'$_6$R'$_7$ with R'$_5$ having the same meaning as R'$_3$; R'$_6$ and R'$_7$ have the same meaning as R'$_3$ and are other than a hydrogen atom, with the proviso that when n>1, the radicals R' may be different from each other, W$_1$ is an aromatic heterocyclic radical chosen from the following radicals:

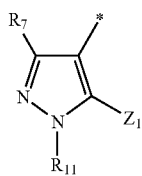 (RI)

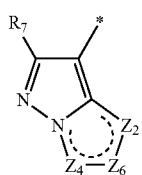 (RII)

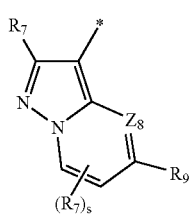 (RIII)

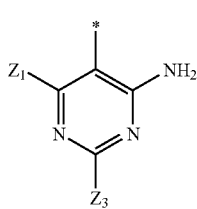 (RIV)

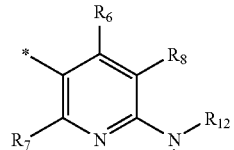 (RV)

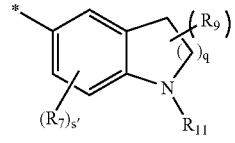 (RVI)

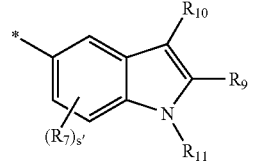 (RVII)

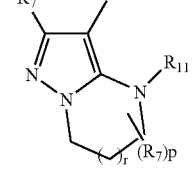 (RVIII)

in which s is 0, 1 or 2, s' is 0, 1, 2 or 3,

Z$_1$ and Z$_3$ are chosen from, independently of each other, a hydroxyl radical and NR$_{11}$R$_{12}$ radicals, Z$_2$, Z$_4$ and Z$_6$ are chosen from, independently of each other, a nitrogen atom, CR$_{12}$ radicals, and NR$_{11}$ radicals, with the proviso that at least one of Z$_2$, Z$_4$ and Z$_6$ is chosen from a radical CR$_{12}$ and that there are not more than three contiguous nitrogen atoms, Z$_8$ is chosen from a nitrogen atom and a radical CR$_{12}$, R$_6$ and R$_8$, independently of each other, have the same meanings as R$_3$, R$_7$, R$_9$, R$_{10}$, R$_{11}$ and R$_{12}$ are chosen from, independently of each other:

a hydrogen atom, linear or branched C$_1$-C$_{10}$ hydrocarbon-based chains, which can form at least one 5- to 8-membered carbon-based ring, and which may be saturated or unsaturated, wherein at least one carbon atom of the carbon-based chain may be replaced with at least one entity chosen from oxygen, nitrogen and sulfur atoms and SO$_2$ groups, and wherein the carbon atoms may be, independently of each other, substituted with at least one halogen atom; the radicals R$_7$ and R$_9$ to R$_{12}$ not comprising a peroxide bond or diazo or nitroso radicals, and the radicals R$_{11}$ and R$_{12}$ not being directly linked to the nitrogen atom via an oxygen, sulfur or nitrogen atom, with the proviso that the radicals R$_7$ and R$_9$ may be independent of each other, p ranges from 4 to 8, q ranges from 1 to 3, and r ranges from 0 to 2,

* indicates the point of attachment of W$_1$ in formula (I), with the proviso that the compound of formula (I) cannot comprise more than one cationic radical D1-Z.

* * * * *